United States Patent
Gebert-Schwarzwaelder et al.

(10) Patent No.: US 9,636,288 B2
(45) Date of Patent: May 2, 2017

(54) MEANS FOR OXIDATIVE DYEING OF KERATIN FIBERS CONTAINING NOVEL TETRA-SUBSTITUTED DERIVATIVES OF PYRIMIDINE

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Melanie Moch, Dormagen (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 15/184,648

(22) Filed: Jun. 16, 2016

(65) Prior Publication Data
US 2016/0296447 A1 Oct. 13, 2016

Related U.S. Application Data

(63) Continuation of application No. PCT/DE2014/200506, filed on Sep. 25, 2014.

(30) Foreign Application Priority Data

Dec. 19, 2013 (DE) ........................ 10 2013 226 585

(51) Int. Cl.
*A61Q 5/10* (2006.01)
*A61K 8/49* (2006.01)
*B65D 81/32* (2006.01)

(52) U.S. Cl.
CPC .............. *A61K 8/4953* (2013.01); *A61Q 5/10* (2013.01); *B65D 81/32* (2013.01); *A61K 2800/4324* (2013.01); *A61K 2800/88* (2013.01)

(58) Field of Classification Search
CPC .... A61Q 5/10; A61K 8/4953; A61K 2800/88; A61K 2800/4324; B65D 81/32
See application file for complete search history.

(56) References Cited

U.S. PATENT DOCUMENTS

| 8,900,329 B2 | 12/2014 | Schulze zur Wiesche et al. |
| 2005/0257333 A1 | 11/2005 | Noecker et al. |
| 2006/0156481 A1 | 7/2006 | Lim |

FOREIGN PATENT DOCUMENTS

EP  1598047 A1  11/2005

OTHER PUBLICATIONS

STIC Search Report dated Aug. 23, 2016.*
PCT International Search Report (PCT/DE2014/200506) dated Jan. 12, 2014.

* cited by examiner

*Primary Examiner* — Eisa Elhilo
(74) *Attorney, Agent, or Firm* — David K. Benson

(57) ABSTRACT

Agents for oxidatively dyeing keratinous fibers include, in a cosmetic carrier, as an oxidation dye precursor of the developer type, at least one compound of formula (I) as set forth herein, in which $R^1$, $R^2$ can stand independently of each other, for a hydrogen atom, different substituted alkyl groups, and/or different substituted acrylic groups, and Y stands for a hydroxyl group, an amino group, or a $C_1$-$C_6$ alkylamino group, with the proviso that at least one of the moieties from the group $R^1$ and $R^2$ does not stand for a hydrogen atom, and/or the physiologically compatible salt thereof.

13 Claims, No Drawings

MEANS FOR OXIDATIVE DYEING OF KERATIN FIBERS CONTAINING NOVEL TETRA-SUBSTITUTED DERIVATIVES OF PYRIMIDINE

FIELD OF THE INVENTION

The present invention generally relates to an agent for oxidatively dyeing keratin-containing fibers, in particular human hair, including at least one tetra-substituted derivative of pyrimidine as an oxidation dye precursor of the developer type. The present invention also relates to a multicomponent packaging unit which includes such above-mentioned agent, and the use of such an agent for improving the leveling properties, light fastness, and wash fastness of oxidative colorings.

BACKGROUND OF THE INVENTION

Changing the shape and color of hair represents an important area of modern cosmetics. For stylish coloring of hairstyles or for concealing gray or even white hair with fashionable or natural hues, the consumer turns to color-changing agents.

For changing the color of keratinic fibers, in particular human hair, those skilled in the art are familiar with various systems, depending on the requirements for the coloring or the change in color.

So-called oxidation dyes are used for long-lasting, intensive colorings having appropriate fastness properties. Such coloring agents customarily include oxidation dye precursors, so-called developer components and coupler components. The developer components form the actual dyes with one another under the influence of oxidizing agents or atmospheric oxygen, or by coupling with one or more coupler components. The oxidation dyes are generally characterized by intensive, excellent, long-lasting color results. For naturally acting colorings, a mixture of a fairly large number of oxidation dye precursors may be used; in many cases, direct dyes are additionally used for shading.

Despite their advantageous coloring properties, oxidative hair dyes have drawbacks. In particular for some of the common oxidation dye precursors, including p-phenylenediamine, it is suspected that for many consumers they may have an irritating effect and thus cause sensitization or even allergic reactions. Therefore, for these substances there is a need for further improvement with regard to their physiological compatibility profile. Many compounds have been investigated in the search for replacement substances, but these often have application-related problems, in particular insufficient leveling properties. In addition, despite the existence of highly developed coloring systems, there is still a need for coloring systems which achieve excellent luminosity and intensity of coloration, and which do not lose these properties even under the effect of external environmental influences such as irradiation by sunlight or washing the hair.

It is therefore desirable to reduce the above-mentioned disadvantages of oxidative hair coloring agents. The coloring agents should produce intensive colorings with high color intensity and good resistance to external influences, in particular with good light fastness and wash fastness, and which do not experience lightening or shifting of the color, even after intensive irradiation with sunlight and multiple shampooings of the hair. Furthermore, the colorings should preferably have excellent leveling properties and should be less selective, i.e., achieve preferably uniform, consistent color results on hair which has been pretreated in various ways. In addition, the coloring agents should have a toxicologically advantageous profile.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for oxidatively dyeing keratinic fibers, including in a cosmetic carrier at least one compound of formula (I) as an oxidation dye precursor of the developer type:

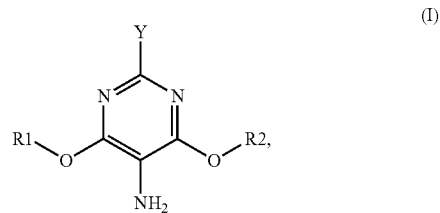

(I)

in which $R^1$, $R^2$ independently stand for a hydrogen atom, a $C_1$-$C_6$ alkyl group, a $C_2$-$C_6$ alkenyl group, a hydroxy-$C_1$-$C_6$ alkyl group, a polyhydroxy-$C_2$-$C_6$ alkyl group, a $C_1$-$C_6$ alkoxy-$C_1$-$C_6$ alkyl group, a hydroxy-$C_1$-$C_6$ alkyoxy-$C_1$-$C_6$ alkyl group, a $C_1$-$C_6$ alkoxy-$C_1$-$C_6$ alkyl group, a carboxy-$C_1$-$C_6$ alkyl group, a $C_1$-$C_6$ alkanoyl group, a $C_1$-$C_6$ alkoxycarbonyl group, a $C_1$-$C_6$ alkylaminocarbonyl group, a (di-$C_1$-$C_6$ alkylamino)carbonyl group, an aryl group, a heteroaryl group, or a $(R^3R^4N)$—$C_2$-$C_6$ alkyl group, where $R^3$, $R^4$ independently stand for a hydrogen atom, a $C_1$-$C_6$ alkyl group, a hydroxy-$C_1$-$C_6$ alkyl group, an amino-$C_1$-$C_6$ alkyl group, a $C_1$-$C_6$ alkoxy-$C_1$-$C_6$ alkyl group, an aryl group, or a heteroaryl group; Y stands for a hydroxy group, an amino group, or a $C_1$-$C_6$ alkylamino group, with the condition that at least one of the moieties from the group $R^1$ and $R^2$ does not stand for a hydrogen atom; and/or the physiologically acceptable salt thereof.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that certain tetra-substituted pyrimidine derivatives are very well suited as oxidation dye precursors of the developer type for dyeing keratin-containing fibers. Intensive colorings having good leveling properties, good light fastness, and good wash fastness, in particular in the range of fashionable red, reddish-brown, and violet shades, may be produced using the novel pyrimidine derivatives.

The invention firstly relates to an agent for oxidatively dyeing keratinic fibers, including in a cosmetic carrier at least one compound of formula (I) as an oxidation dye precursor of the developer type:

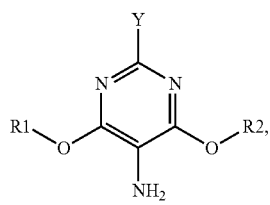

(I)

in which
R[1], R[2] independently stand for a hydrogen atom, a $C_1$-$C_6$ alkyl group, a $C_2$-$C_6$ alkenyl group, a hydroxy-$C_1$-$C_6$ alkyl group, a polyhydroxy-$C_2$-$C_6$ alkyl group, a $C_1$-$C_6$ alkoxy-$C_1$-$C_6$ alkyl group, a hydroxy-$C_1$-$C_6$ alkyoxy-$C_1$-$C_6$ alkyl group, a $C_1$-$C_6$ alkoxy-$C_1$-$C_6$ alkyl group, a carboxy-$C_1$-$C_6$ alkyl group, a $C_1$-$C_6$ alkanoyl group, a $C_1$-$C_6$ alkoxycarbonyl group, a $C_1$-$C_6$ alkylaminocarbonyl group, a (di-$C_1$-$C_6$ alkylamino)carbonyl group, an aryl group, a heteroaryl group, or a (R[3]R[4]N)—$C_2$-$C_6$ alkyl group,
where
R[3], R[4] independently stand for a hydrogen atom, a $C_1$-$C_6$ alkyl group, a hydroxy-$C_1$-$C_6$ alkyl group, an amino-$C_1$-$C_6$ alkyl group, a $C_1$-$C_6$ alkoxy-$C_1$-$C_6$ alkyl group, an aryl group, or a heteroaryl group,
Y stands for a hydroxy group, an amino group, or a $C_1$-$C_6$ alkylamino group, with the condition that at least one of the moieties from the group R[1] and R[2] does not stand for a hydrogen atom,
and/or the physiologically acceptable salt thereof.

Keratinic fibers are understood to mean fur, wool, feathers, and in particular human hair. In principle, however, the coloring agents according to the invention may also be used for dyeing other natural fibers, for example cotton, jute, sisal, linen, or silk, and modified natural fibers such as regenerated cellulose or nitro-, alkyl-, hydroxyalkyl-, or acetylcellulose.

The agents according to the invention include the compounds of formula (I) in a cosmetic carrier, preferably in a suitable aqueous, alcoholic, or aqueous-alcoholic carrier. For purposes of the hair coloring, such carriers are, for example, creams, emulsions, gels, or also surfactant-containing foaming solutions such as shampoos, foam aerosols, foam formulations, or other preparations that are suitable for application to the hair. However, it is also conceivable to integrate the dye precursors according to formula (I) into a powdered or also a tablet formulation. Within the meaning of the present invention, aqueous-alcoholic solutions are understood to mean aqueous solutions including 3 to 70% by weight of a $C_1$-$C_4$ alcohol, in particular ethanol or isopropanol. The agents according to the invention may additionally include further organic solvents, for example methoxybutanol, benzyl alcohol, ethyl diglycol, or 1,2-propylene glycol. All water-soluble organic solvents are preferred.

Examples of R1, R2, R3, and R4 stated in formula (I) are listed below:

Examples of $C_1$-$C_6$ alkyl moieties are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Methyl and ethyl are particularly preferred alkyl moieties. Examples of $C_2$-$C_6$ alkenyl groups are prop-2-enyl (allyl group), 2-methyl-prop-2-enyl, but-3-enyl, but-2-enyl, pent-4-enyl, or pent-3-enyl. Examples of $C_1$-$C_6$ hydroxyalkyl groups are —$CH_2OH$, —$CH_2CH_2OH$, —$CH_2CH_2CH_2OH$, —$CH_2CH(OH)CH_3$, —$CH_2CH_2CH_2CH_2OH$, with —$CH_2CH_2OH$ being preferred. Examples of $C_2$-$C_6$ polyhydroxyalkyl groups are the 2,3-dihydroxypropyl group, the 3,4-dihydroxybutyl group, the 2,4-dihydroxybutyl group, and the 1,2-dihydroxyethyl group. Possible examples of a $C_1$-$C_6$ alkoxy-$C_1$-$C_6$ alkyl group are the groups $H_3C$—O—$CH_2$—, $H_3C$—O—$CH_2$—$CH_2$—, $H_3C$—O—$CH_2$—$CH_2$—$CH_2$—, $H_3C$—$CH_2$—O—$CH_2$—, $H_3C$—$CH_2$—O—$CH_2$—$CH_2$—, and $H_3C$—$CH_2$—O—$CH_2$—$CH_2$—$CH_2$—, with the groups $H_3C$—O—$CH_2$—$CH_2$— and $H_3C$—$CH_2$—O—$CH_2$—$CH_2$— being preferred. Examples of a hydroxy $C_1$-$C_6$ alkyoxy-$C_1$-$C_6$ alkyl group are the groups OH—$CH_2$—O—$CH_2$—, OH—$CH_2$—$CH_2$—O—$CH_2$—, OH—$CH_2$—O—$CH_2$—$CH_2$—, and OH—$CH_2$—$CH_2$—O—$CH_2$—$CH_2$—, with the group OH—$CH_2$—$CH_2$—O—$CH_2$—$CH_2$— being preferred.

Examples of a $C_1$-$C_6$ alkoxy-$C_1$-$C_6$-alkoxy-$C_1$-$C_6$ alkyl group are the groups $H_3C$—O—$CH_2$—O—$CH_2$—, $H_3C$—O—$CH_2$—$CH_2$—O—$CH_2$—$CH_2$—, $H_3C$—$CH_2$—O—$CH_2$—$CH_2$—O—$CH_2$—$CH_2$—, $H_3C$—O—$CH_2$—$CH_2$—$CH_2$—O—$CH_2$—$CH_2$—$CH_2$—, $H_3C$—$CH_2$—O—$CH_2$—$CH_2$—O—$CH_2$—$CH_2$—.

Examples of a carboxy-$C_1$-$C_6$ alkyl group are the groups HOOC—$CH_2$—, HOOC—$CH_2$—$CH_2$—, and HOOC—$CH_2$—$CH_2$—$CH_2$—, with the group HOOC—$CH_2$— (i.e., a carboxymethyl group) being particularly preferred. A particularly preferred $C_1$-$C_6$ alkanoyl group is the acetyl group ($H_3C$—C(O)—). The groups $H_3C$—O—C(O)— and $H_3C$—$CH_2$—O—C(O)— may be named as examples of a $C_1$-$C_6$ alkoxycarbonyl group.

Examples of a $C_1$-$C_6$ alkylaminocarbonyl group are the groups $H_3C$—NH—C(O)— and $H_3C$—$CH_2$—NH—C(O)—. Examples of a (di-$C_1$-$C_6$ alkylamino)carbonyl group are the groups $(H_3C)_2N$—C(O)—, $(H_3C$—$CH_2)_2N$—C(O)—, and $(H_3C$—$CH_2$—$CH_2)_2N$—C(O)—. The phenyl group may be named in particular as an example of an aryl group. Examples of a heteroaryl group are in particular the pyridin-2-yl group, the pyridin-3-yl group, the pyridin-4-yl group, and the imidazol-2-yl group. Examples of $C_1$-$C_6$ alkoxy groups are —$OCH_3$, —$OCH_2CH_3$, —$OCH_2CH_2CH_3$, —$OCH(CH_3)_2$ or —$OC(CH_3)_3$, with the methoxy group (—$OCH_3$) being preferred. Examples of an amino $C_1$-$C_6$ alkyl group are the groups $H_2N$—$CH_2$—, $H_2N$—$CH_2$—$CH_2$—, and $H_2N$—$CH_2$—$CH_2$—$CH_2$—.

Within the group of tetra-substituted pyrimidine derivatives according to the invention, certain substitution patterns show particularly advantageous properties. In particular compounds of formula (I), in which the moieties R1 and/or R2 independently stand for a $C_1$-$C_6$ alkyl group, a hydroxy $C_1$-$C_6$ alkyl group, a $C_1$-$C_6$ alkoxy-$C_1$-$C_6$ alkyl group, a C1-$C_6$ alkanoyl group, a $C_1$-$C_6$ alkoxycarbonyl group, or an aryl group, are well absorbed into the keratin fiber. Within this embodiment, it is very particularly preferred when R1 and R2 in each case independently stand for a $C_1$-$C_6$ alkyl group, since the highest color intensity is observed for appropriately substituted compounds of formula (I).

A particularly preferred agent for oxidatively dyeing keratinic fibers is therefore characterized in that it includes at least one compound of formula (I), in which R[1] and R[2] independently stand for a $C_1$-$C_6$ alkyl group, a hydroxy $C_1$-$C_6$ alkyl group, a $C_1$-$C_6$ alkoxy-$C_1$-$C_6$ alkyl group, a $C_1$-$C_6$ alkanoyl group, a $C_1$-$C_6$ alkoxycarbonyl group, or an aryl group, particularly preferably a $C_1$-$C_6$ alkyl group.

In the course of the studies leading to the present invention, it has also been found that compounds of formula (I)

have extremely good application-related properties when the moiety Y stands for a hydroxy group or an amino group.

A particularly preferred agent for oxidatively dyeing keratinic fibers is further characterized in that it includes at least one compound of formula (I), in which Y stands for a hydroxy group or an amino group.

Accordingly, an agent for oxidatively dyeing keratinic fibers is particularly preferred which includes in a cosmetic carrier at least one compound of formula (I) as an oxidation dye precursor of the developer type:

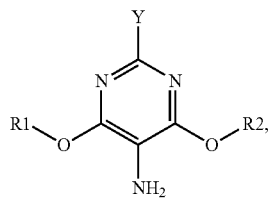

(I)

in which
R¹, R² independently stand for a $C_1$-$C_6$ alkyl group,
Y stands for a hydroxy group or an amino group,
and/or the physiologically acceptable salt thereof.

In the investigation of the fastness properties of agents dyed on keratin fibers, it has been shown that the best wash fastness and the best light fastness can be achieved when a compound of formula (I) is used for the dyeing, in which the moiety R1 stands for a methyl group or an ethyl group, the moiety R2 stands for a methyl group or an ethyl group, and the moiety Y stands for an amino group.

An explicitly very particularly preferred agent for oxidatively dyeing keratinic fibers is therefore characterized in that R¹ and R² both stand for a methyl group and Y stands for an amino group.

An explicitly very particularly preferred agent for oxidatively dyeing keratinic fibers is also characterized in that R¹ and R² both stand for an ethyl group and Y stands for an amino group.

Taking the above-mentioned embodiments into account, an agent for oxidatively dyeing keratinic fibers is therefore preferred which includes at least one of the following compounds of formula (I):

2,5-Diamino-6-methoxypyrimidin-4-ol

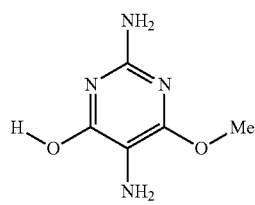 [SMILES: COc1nc(N)nc(O)c1N]

2,5-Diamino-6-ethoxypyrmidin-4-ol

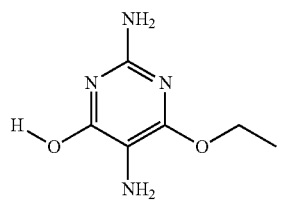

2,5-Diamino-6-propoxypyrimidin-4-ol

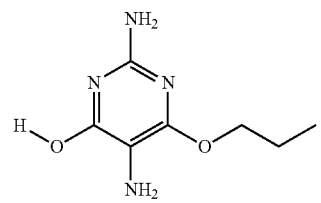

2,5-Diamino-6-(2-methylpropoxy)pyrimidin-4-ol

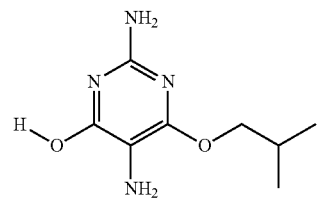

4,6-Dimethoxypyrimidine-2,5-diamine

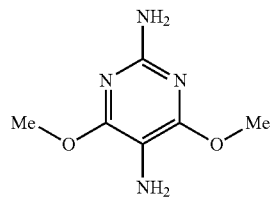 [SMILES: COc1nc(N)nc(OC)c1N]

4-Methoxy-6-ethoxypyrimidine-2,5-diamine

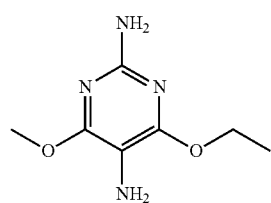

4-Methoxy-6-propoxypyrimidine-2,5-diamine

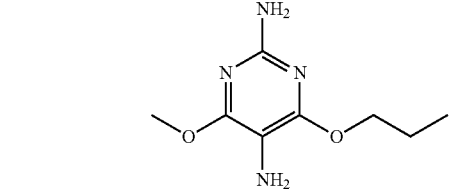

4-Methoxy-6-(2-methylpropoxy)pyrimidine-2,5-diamine 4,6-Diethoxypyrimidine-2,5-diamine

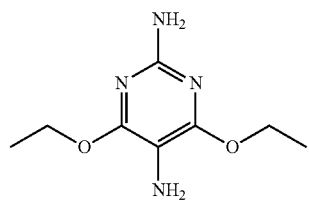

4-Ethoxy-6-propoxypyrimidine-2,5-diamine

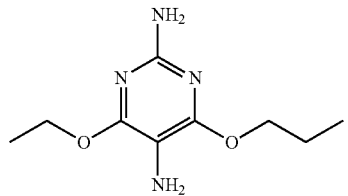

4-Ethoxy-6-(2-methylpropoxy)pyrimidine-2,5-diamine

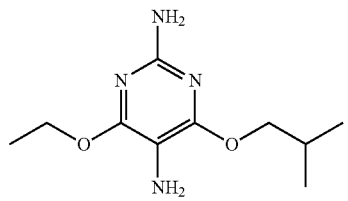 [SMILES: CCOc1nc(N)nc(OCC(C)C)c1N]

4-(Ethenyloxy)-6-methoxypyrimidine-2,5-diamine

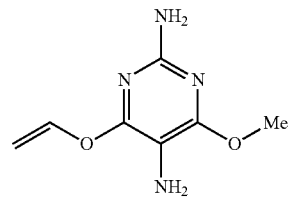

4-(Ethenyloxy)-6-ethoxypyrimidine-2,5-diamine

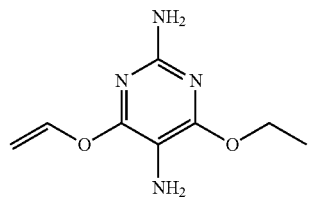

4-(Ethenyloxy)-6-propoxypyrimidine-2,5-diamine

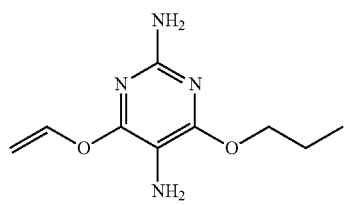

4-(Ethenyloxy)-6-(2-methylpropoxy)pyrimidine-2,5-diamine

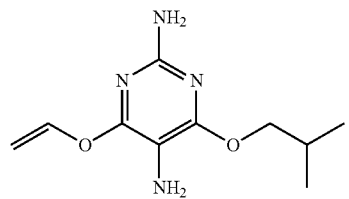 [SMILES: C=COc1nc(N)nc(OCC(C)C)c1N]

4-Methoxy-6-(prop-2-en-1-yloxy)pyrimidine-2,5-diamine

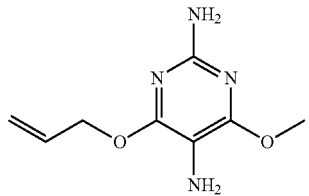

4-Ethoxy-6-(prop-2-en-1-yloxy)pyrimidine-2,5-diamine

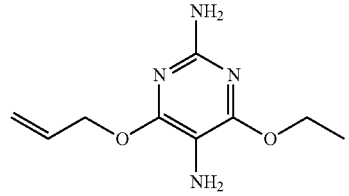

4-(2-Methylpropoxy)-6-(prop-2-en-1-yloxy)pyrimidine-2,5-diamine

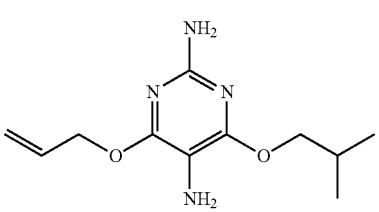 [SMILES: C=CCOc1nc(N)nc(OCC(C)C)c1N]

[(2,5-Diamino-6-methoxypyrimidin-4-yl)oxy]methanol

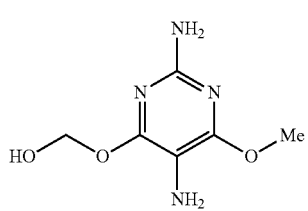 [SMILES: COc1nc(N)nc(OCO)c1N]

[(2,5-Diamino-6-ethoxypyrimidin-4-yl)oxy]methanol

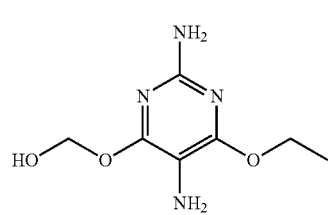

| 9 | 10 |
|---|---|
| [(2,5-Diamino-6-propoxypyrimidin-4-yl)oxy]methanol | [(2,5-Diamino-6-propoxypyrimidin-4-yl)oxy)]ethanol |

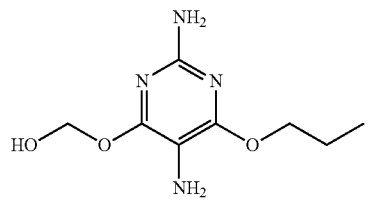

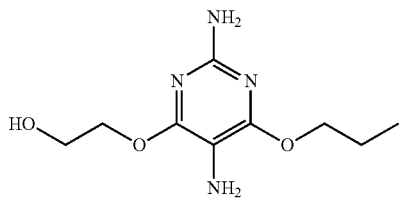

[(2,5-Diamino-6-(2-methylpropoxy)pyrimidin-4-yl)oxy]methanol

[(2,5-Diamino-6-(2-methylpropoxy)pyrimidin-4-yl)oxy]ethanol

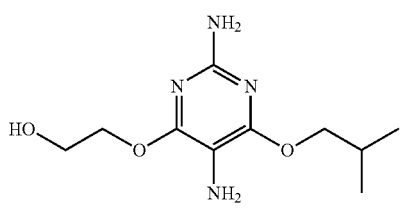

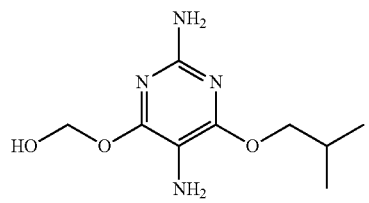 [SMILES: CC(C)COc1nc(N)nc(OCO)c1N]

{[2,5-Diamino-6-(hydroxymethoxy)pyrimidin-4-yl]oxy}methanol

2-{[2,5-Diamino-6-(2-hydroxyethoxy)pyrimidin-4-yl]oxy}ethan-1-ol

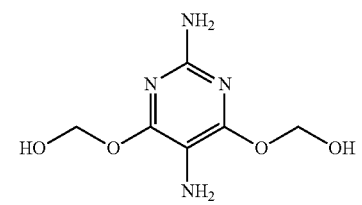 [SMILES: Nc1nc(OCO)c(N)c(OCO)n1]

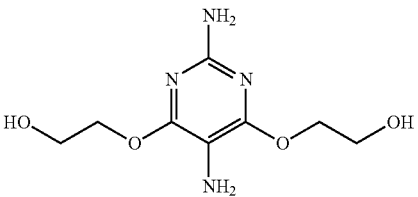

[(2,5-Diamino-6-methoxypyrimidin-4-yl)oxy]ethanol

[(2,5-Diamino-6-methoxypyrimidin-4-yl)oxy]propanol

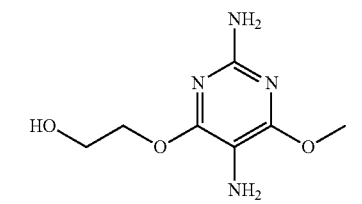

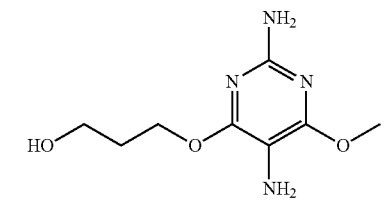

[(2,5-Diamino-6-ethoxypyrimidin-4-yl)oxy]ethanol

[(2,5-Diamino-6-ethoxypyrimidin-4-yl)oxy]propanol

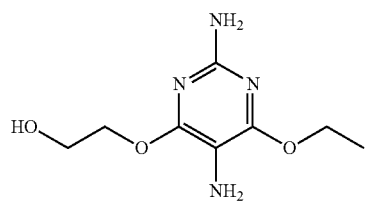

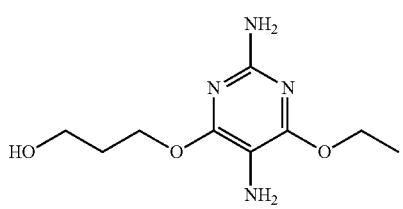 [SMILES: CCOc1nc(N)nc(OCCCO)c1N]

| 11 | 12 |
|---|---|
| [(2,5-Diamino-6-propoxypyrimidin-4-yl)oxy]propanol | [(2,5-Diamino-6-propoxypyrimidin-4-yl)oxy]methoxy)methanol |
| 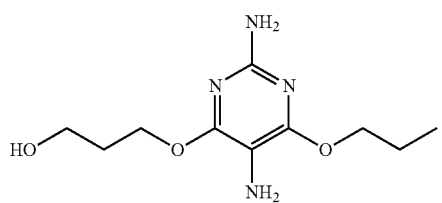 [SMILES: CCCOc1nc(N)nc(OCCCO)c1N] | 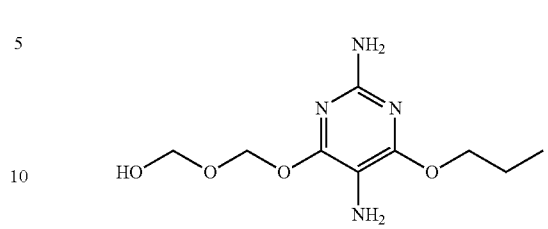 |
| [(2,5-Diamino-6-(2-methylpropoxy)pyrimidin-4-yl)oxy]propanol | [(2,5-Diamino-6-(2-methylpropoxy)pyrimidin-4-yl)oxy]methoxy)methanol |
| 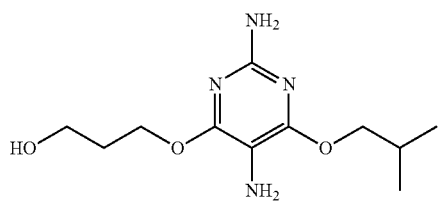 [SMILES: CC(C)COc1nc(N)nc(OCCCO)c1N] | 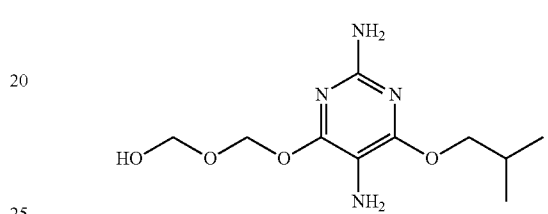 |
| [(2,5-Diamino-6-(2-hydroxypropoxy)pyrimidin-4-yl)oxy]propanol | [(2,5-Diamino-6-[(hydroxymethoxy)methoxy]pyrimidin-4-yl)oxy]methoxy)methanol |
| 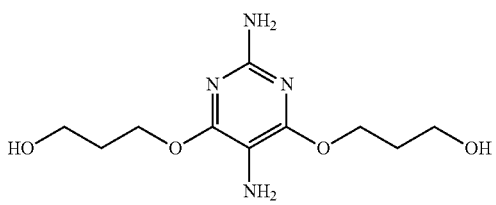 [SMILES: Nc1nc(OCCCO)c(N)c(OCCCO)n1] | 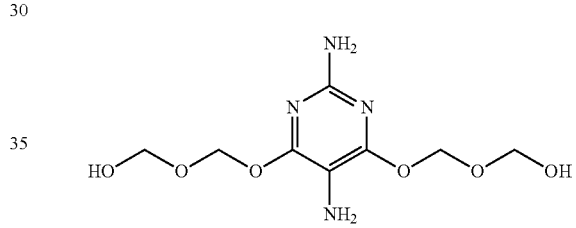 |
| [(2,5-Diamino-6-methoxypyrimidin-4-yl)oxy]methoxy)methanol | 2-{2-[(2,5-Diamino-6-methoxypyrimidin-4-yl)oxy]ethoxy}ethan-1-ol |
| 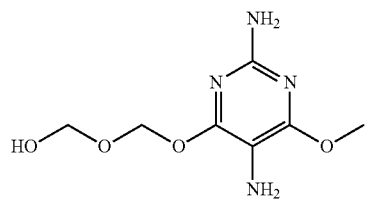 | 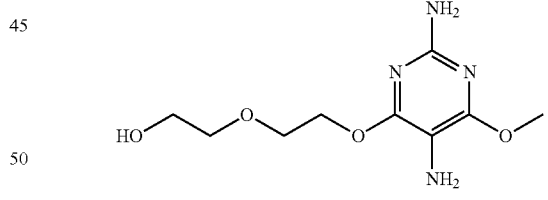 |
| [(2,5-Diamino-6-ethoxypyrimidin-4-yl)oxy]methoxy)methanol | 2-{2-[(2,5-Diamino-6-ethoxypyrimidin-4-yl)oxy]ethoxy}ethan-1-ol |
| 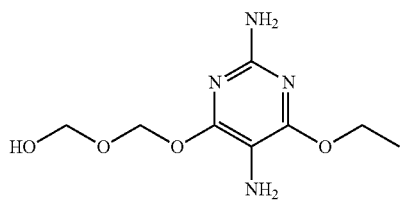 | 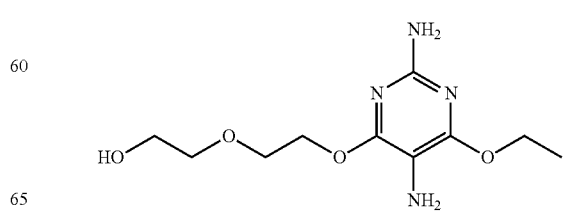 |

2-{2-[(2,5-Diamino-6-methoxypyrimidin-4-yl)oxy]ethoxy}ethan-1-ol

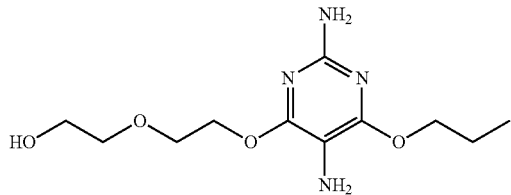 [SMILES: CCCOc1nc(N)nc(OCCOCCO)c1N]

2-(2-{[2,5-diamino-6-(2-methylpropoxy)pyrimidin-4-yl]oxy}ethoxy)ethan-1-ol

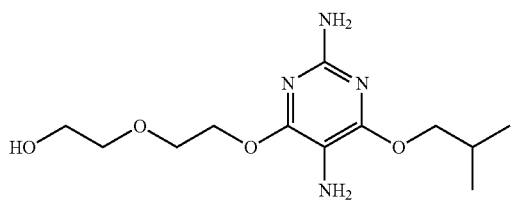 [SMILES: CC(C)COc1nc(N)nc(OCCOCCO)c1N]

2-{2-[(2,5-Diamino-6-[(hydroxyethoxy)ethoxy]pyrimidin-4-yl)oxy]ethoxy}ethan-1-ol

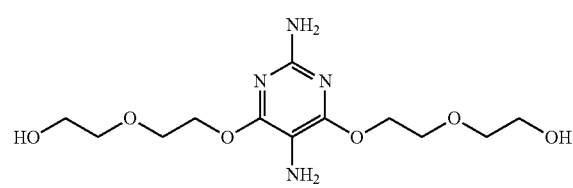 [SMILES: Nc1nc(OCCOCCO)c(N)c(OCCOCCO)n1]

2,5-Diamino-6-methoxypyrimidin-4-yl acetate

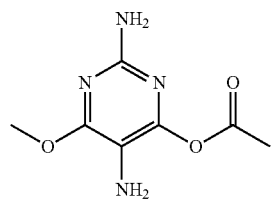

2,5-Diamino-6-ethoxypyrimidin-4-yl acetate

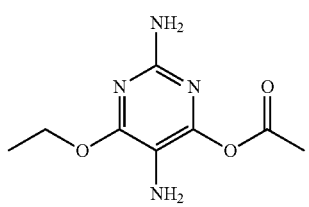

2,5-Diamino-6-propoxypyrimidin-4-yl acetate

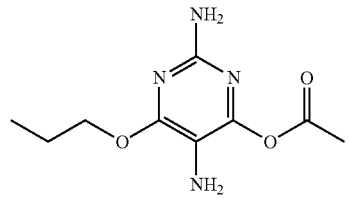

2,5-Diamino-6-(2-methylpropoxy)pyrimidin-4-yl acetate

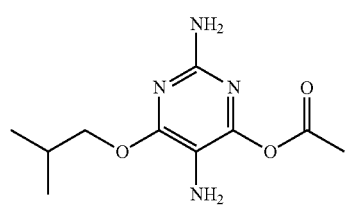 [SMILES: CC(=O)Oc1nc(N)nc(OCC(C)C)c1N]

6-(Acetyloxy)-2,5-diaminopyrimidin-4-yl acetate

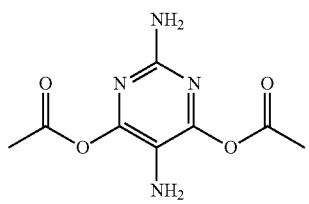 [SMILES: CC(=O)Oc1nc(N)nc(OC(C)=O)c1N]

2,5-Diamino-6-methoxypyrimidin-4-yl propanoate

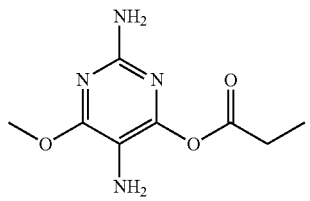

2,5-Diamino-6-ethoxypyrimidin-4-yl propanoate

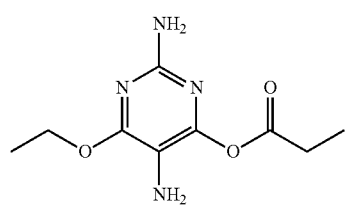

15
2,5-Diamino-6-propoxypyrimidin-4-yl propanoate

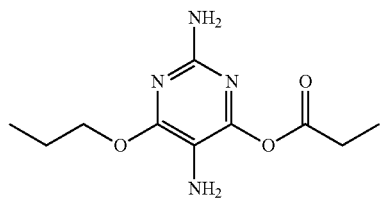 [SMILES: CCCOc1nc(N)nc(OC(=O)CC)c1N]

2,5-Diamino-6-(2-methylpropoxy)pyrimidin-4-yl propanoate

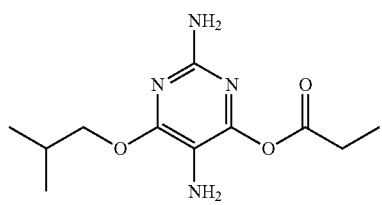

2,5-Diamino-6-(propanoyloxy)pyrimidin-4-yl propanoate

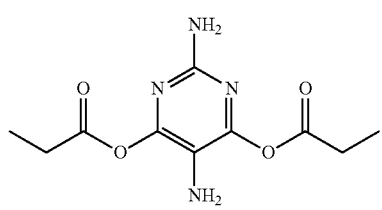 [SMILES: CCC(=O)Oc1nc(N)nc(OC(=O)CC)c1N]

2,5-Diamino-6-methoxypyrimidin-4-yl butanoate

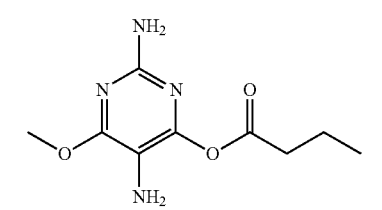 [SMILES: CCCC(=O)Oc1nc(N)nc(OC)c1N]

2,5-Diamino-6-ethoxypyrimidin-4-yl butanoate

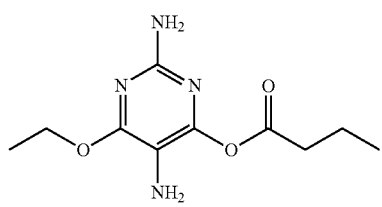

16
2,5-Diamino-6-propoxypyrimidin-4-yl butanoate

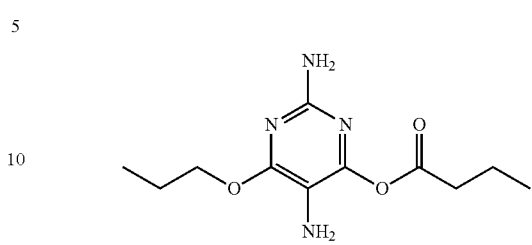

2,5-Diamino-6-(2-methylpropoxy)pyrimidin-4-yl butanoate

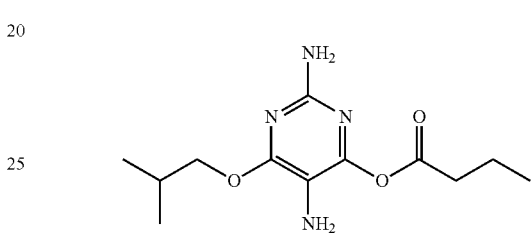

2,5-Diamino-6-(butanoyloxy)pyrimidin-4-yl butanoate

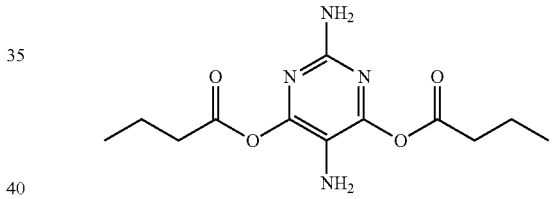

2,5-Diamino-6-methoxypyrimidin-4-yl methyl carbonate

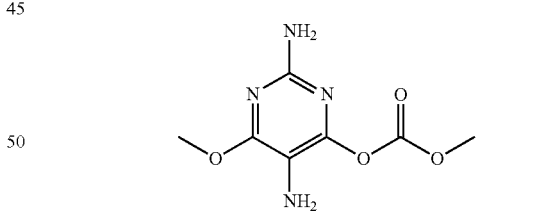

2,5-Diamino-6-ethoxypyrimidin-4-yl methyl carbonate

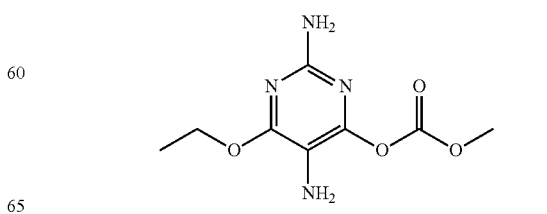

17

2,5-Diamino-6-propoxypyrimidin-4-yl methyl carbonate

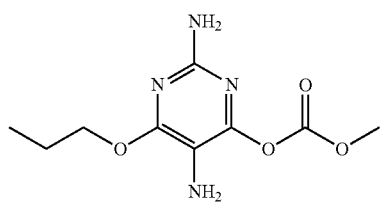 [SMILES: CCCOc1nc(N)nc(OC(=O)OC)c1N]

2,5-Diamino-6-(2-methylpropoxy)pyrimidin-4-yl methyl carbonate

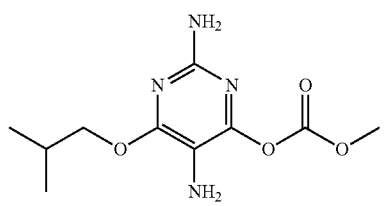 [SMILES: COC(=O)Oc1nc(N)nc(OCC(C)C)c1N]

2,5-Diamino-6-methoxypyrimidin-4-yl ethyl carbonate

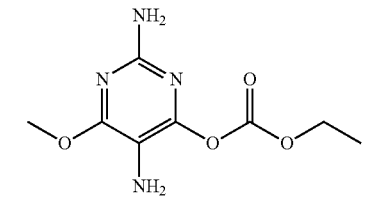 [SMILES: CCOC(=O)Oc1nc(N)nc(OC)c1N]

2,5-Diamino-6-ethoxypyrimidin-4-yl ethyl carbonate

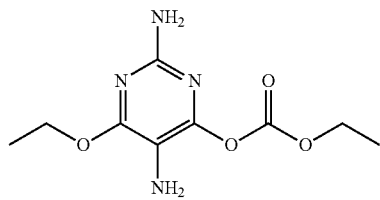 [SMILES: CCOC(=O)Oc1nc(N)nc(OCC)c1N]

2,5-Diamino-6-propoxypyrimidin-4-yl ethyl carbonate

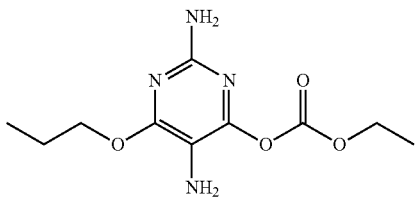 [SMILES: CCCOc1nc(N)nc(OC(=O)OCC)c1N]

18

2,5-Diamino-6-(2-methylpropoxy)pyrimidin-4-yl ethyl carbonate

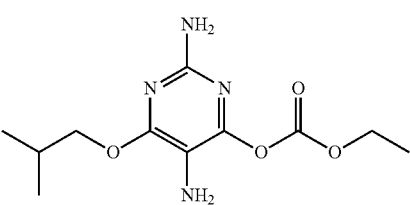

2,5-Diamino-6-methoxypyrimidin-4-yl N-methyl carbamate

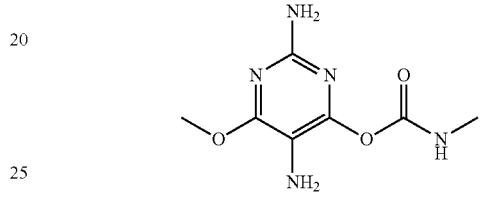

2,5-Diamino-6-ethoxypyrimidin-4-yl N-methyl carbamate

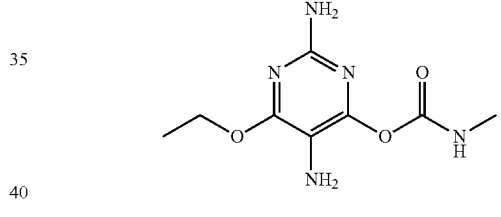

2,5-Diamino-6-propoxypyrimidin-4-yl N-methyl carbamate

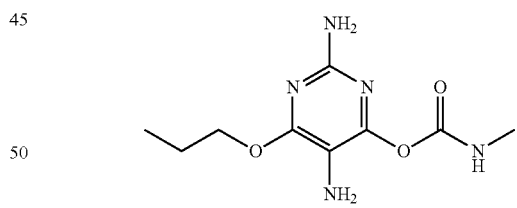

2,5-Diamino-6-(2-methylpropoxy)pyrimidin-4-yl N-methyl carbamate

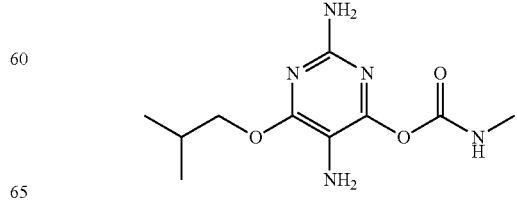

2,5-Diamino-6-methoxypyrimidin-4-yl N-ethyl carbamate

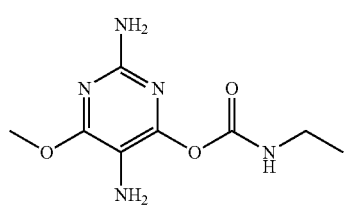 [SMILES: CCNC(=O)Oc1nc(N)nc(OC)c1N]

2,5-Diamino-6-ethoxypyrimidin-4-yl N-ethyl carbamate

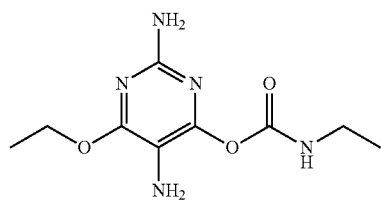 [SMILES: CCNC(=O)Oc1nc(N)nc(OCC)c1N]

2,5-Diamino-6-propoxypyrimidin-4-yl N-ethyl carbamate

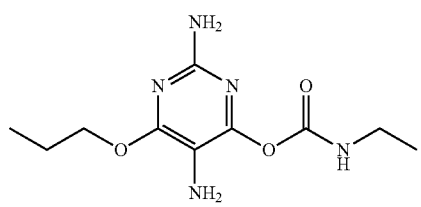 [SMILES: CCCOc1nc(N)nc(OC(=O)NCC)c1N]

2,5-Diamino-6-(2-methylpropoxy)pyrimidin-4-yl N-ethyl carbamate

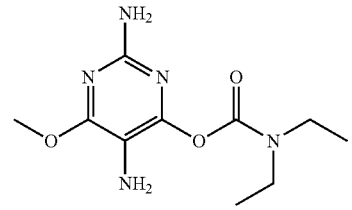

2,5-Diamino-6-methoxypyrimidin-4-yl N,N-dimethyl carbamate

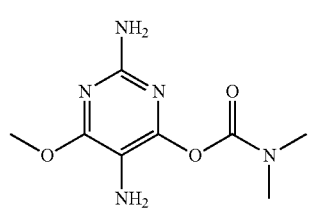

2,5-Diamino-6-ethoxypyrimidin-4-yl N,N-dimethyl carbamate

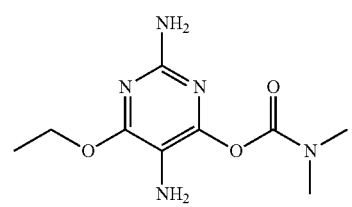 [SMILES: CCOc1nc(N)nc(OC(=O)N(C)C)c1N]

2,5-Diamino-6-propoxypyrimidin-4-yl N,N-dimethyl carbamate

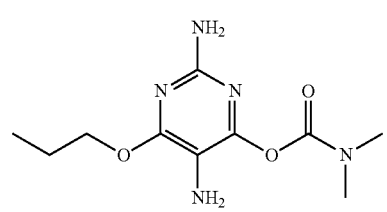 [SMILES: CCCOc1nc(N)nc(OC(=O)N(C)C)c1N]

2,5-Diamino-6-(2-methylpropoxy)pyrimidin-4-yl N,N-dimethyl carbamate

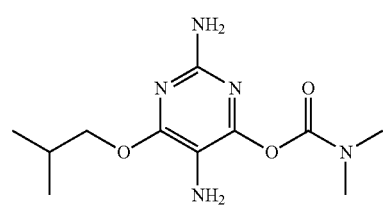 [SMILES: CC(C)COc1nc(N)nc(OC(=O)N(C)C)c1N]

2,5-Diamino-6-methoxypyrimidin-4-yl N,N-diethyl carbamate 2,5-Diamino-6-ethoxypyrimidin-4-yl N,N-diethyl carbamate

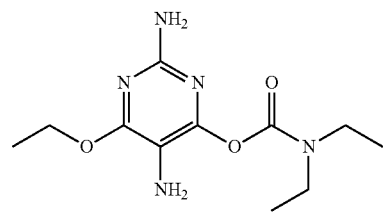 [SMILES: CCOc1nc(N)nc(OC(=O)N(CC)CC)c1N]

21

2,5-Diamino-6-propoxypyrimidin-4-yl N,N-diethyl carbamate

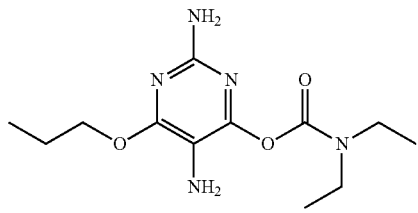 [SMILES: CCCOc1nc(N)nc(OC(=O)N(CC)CC)c1N]

2,5-Diamino-6-(2-methylpropoxy)pyrimidin-4-yl N,N-diethyl carbamate

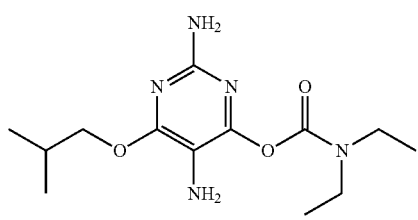 [SMILES: CCN(CC)C(=O)Oc1nc(N)nc(OCC(C)C)c1N]

2,5-Diamino-6-methoxypyrimidin-4-yl N-ethyl-N-methyl carbamate

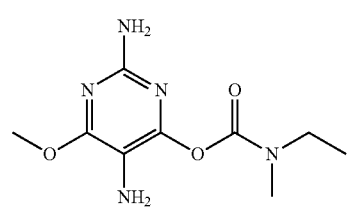

2,5-Diamino-6-ethoxypyrimidin-4-yl N-ethyl-N-methyl carbamate

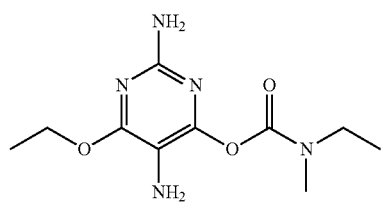

2,5-Diamino-6-propoxypyrimidin-4-yl N-ethyl-N-methyl carbamate

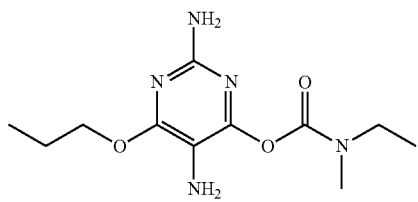 [SMILES: CCCOc1nc(N)nc(OC(=O)N(C)CC)c1N]

22

2,5-Diamino-6-(2-methylpropoxy)pyrimidin-4-yl N-ethyl-N-methyl carbamate

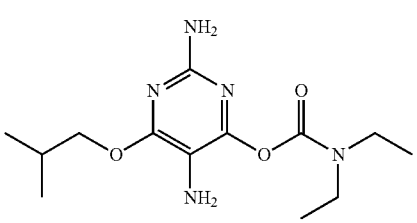 [SMILES: CCN(CC)C(=O)Oc1nc(N)nc(OCC(C)C)c1N]

4-(Aminomethoxy)-6-methoxyprimidine-2,5-diamine

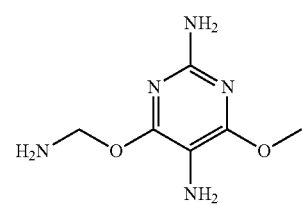

4-(Aminomethoxy)-6-ethoxypyrimidine-2,5-diamine

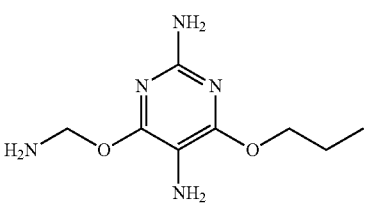

4-(Aminomethoxy)-6-propoxypyrimidine-2,5-diamine 4-(Aminomethoxy)-6-(2-methylpropoxy)pyrimidine-2,5-diamine

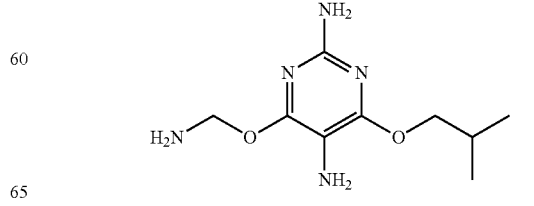

4-(Aminomethoxy)-6-(aminomethoxy)pyrimidine-2,5-diamine

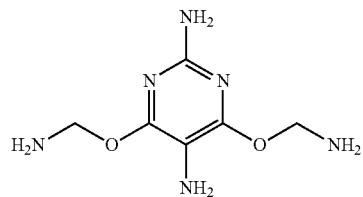 [SMILES: NCOc1nc(N)nc(OCN)c1N]

4-Methoxy-6-[(methylamino)methoxy]pyrimidine-2,5-diamine

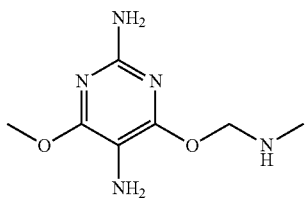

4-Ethoxy-6-[(methylamino)methoxy]pyrimidine-2,5-diamine

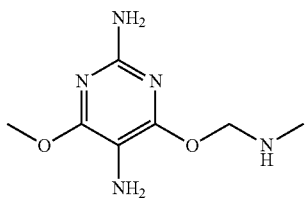

4-Propoxy-6-[(methylamino)methoxy]pyrimidine-2,5-diamine

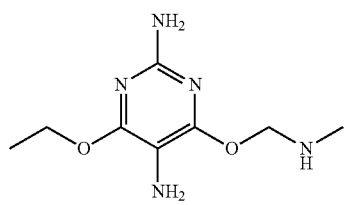

4-(2-Methylpropoxy)-6-[(methylamino)methoxy]pyrimidine-2,5-diamine

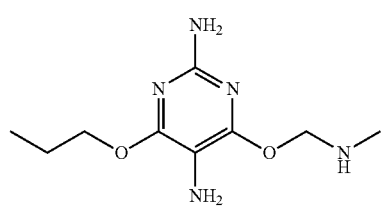 [SMILES: CCCOc1nc(N)nc(OCNC)c1N]

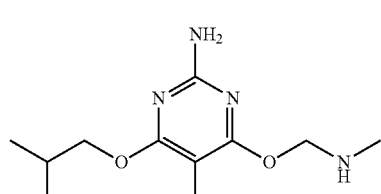

4-[(Dimethylamino)methoxy]-6-methoxypyrimidine-2,5-diamine

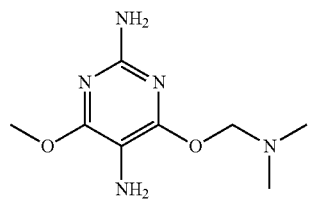

4-[(Dimethylamino)methoxy]-6-ethoxypyrimidine-2,5-diamine

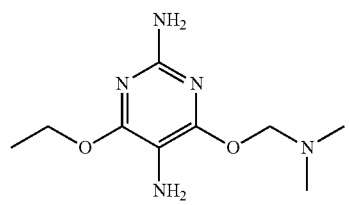

4-[(Dimethylamino)methoxy]-6-propoxypyrimidine-2,5-diamine

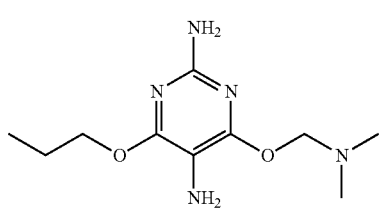 [SMILES: CCCOc1nc(N)nc(OCN(C)C)c1N]

4-[(Dimethylamino)methoxy]-6-(2-methylpropoxy)pyrimidine-2,5-diamine

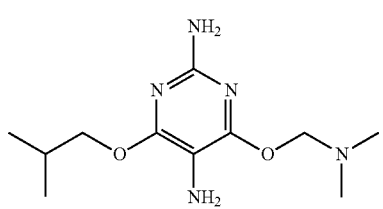 [SMILES: CC(C)COc1nc(N)nc(OCN(C)C)c1N]

4-[(Diethylamino)methoxy]-6-methoxypyrimidine-2,5-diamine

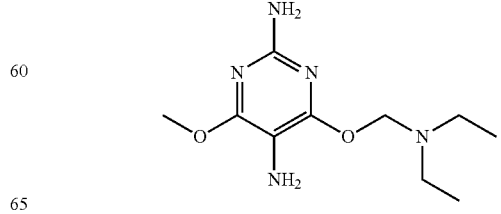

4-[(Diethylamino)methoxy]-6-ethoxypyrimidine-2,5-diamine

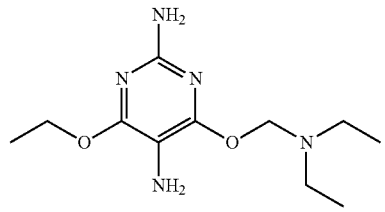 [SMILES: CCOc1nc(N)nc(OCN(CC)CC)c1N]

4-[(Diethylamino)methoxy]-6-propoxypyrimidine-2,5-diamine

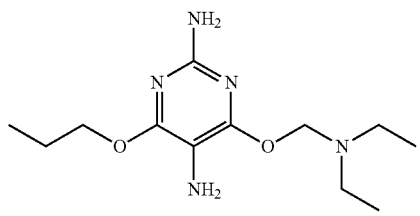 [SMILES: CCCOc1nc(N)nc(OCN(CC)CC)c1N]

4-[(Diethylamino)methoxy]-6-(2-methylpropoxy)pyrimidine-2,5-diamine

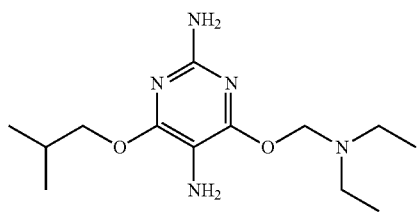 [SMILES: CCN(CC)COc1nc(N)nc(OCC(C)C)c1N]

4-[(Dimethylamino)ethoxy]-6-methoxypyrimidine-2,5-diamine

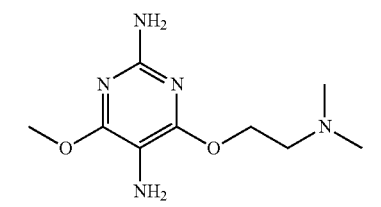

4-[(Dimethylamino)ethoxy]-6-ethoxypyrimidine-2,5-diamine

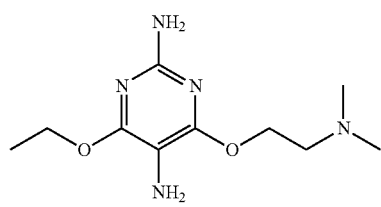 [SMILES: CCOc1nc(N)nc(OCCN(C)C)c1N]

4-[(Dimethylamino)ethoxy]-6-propoxypyrimidine-2,5-diamine

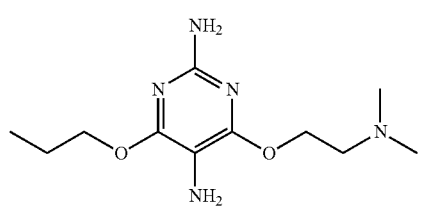 [SMILES: CCCOc1nc(N)nc(OCCN(C)C)c1N]

4-[(Dimethylamino)ethoxy]-6-(2-methylpropoxy)pyrimidine-2,5-diamine

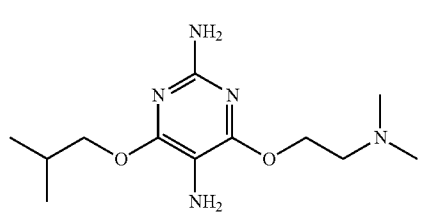 [SMILES: CC(C)COc1nc(N)nc(OCCN(C)C)c1N]

4-[(Diethylamino)ethoxy]-6-methoxyprimidine-2,5-diamine

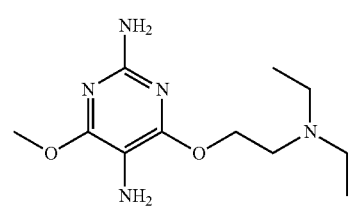 [SMILES: CCN(CC)CCOc1nc(N)nc(OC)c1N]

4-[(Diethylamino)ethoxy]-6-ethoxypyrimidine-2,5-diamine

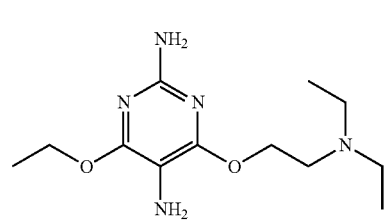 [SMILES: CCOc1nc(N)nc(OCCN(CC)CC)c1N]

4-[(Diethylamino)ethoxy]-6-propoxypyrimidine-2,5-diamine

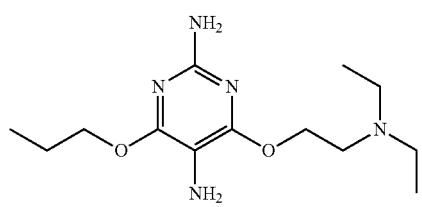 [SMILES: CCCOc1nc(N)nc(OCCN(CC)CC)c1N]

4-[(Diethylamino)ethoxy]-6-(2-methylpropoxy)pyrimidine-2,5-diamine

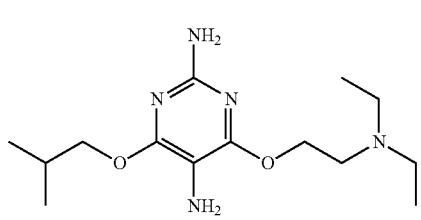 [SMILES: CCN(CC)CCOc1nc(N)nc(OCC(C)C)c1N]

4-(Benzyloxy)-6-methoxypyrimidine-2,5-diamine

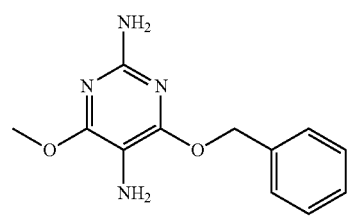 [SMILES: COc1nc(N)nc(OCc2ccccc2)c1N]

4-(Benzyloxy)-6-ethoxypyrimidine-2,5-diamine

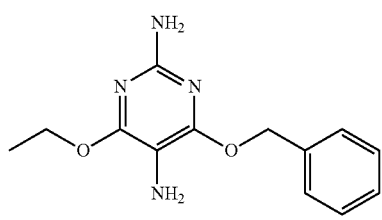 [SMILES: CCOc1nc(N)nc(OCc2ccccc2)c1N]

4-(Benzyloxy)-6-propoxypyrimidine-2,5-diamine

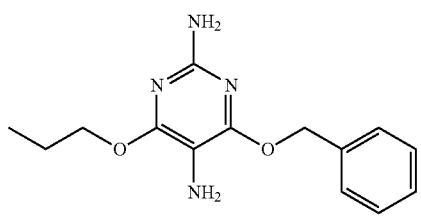 [SMILES: CCCOc1nc(N)nc(OCc2ccccc2)c1N]

4-(Benzyloxy)-6-(2-methylpropoxy)pyrimidine-2,5-diamine

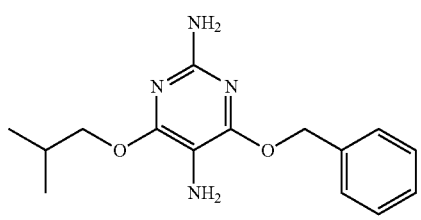 [SMILES: CC(C)COc1nc(N)nc(OCc2ccccc2)c1N]

4,6-Dibenzyloxypyrimidine-2,5-diamine

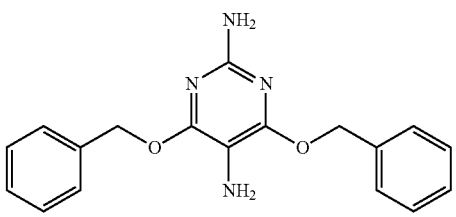 [SMILES: Nc1nc(OCc2ccccc2)c(N)c(OCc2ccccc2)n1]

4-(Benzyloxy)-6-(prop-2-en-1-yloxy)pyrimidine-2,5-diamine

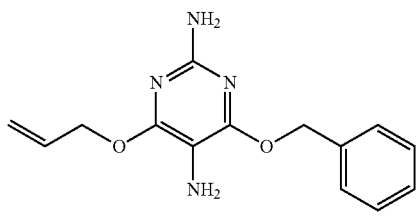 [SMILES: C=CCOc1nc(N)nc(OCc2ccccc2)c1N]

Benzyl 2,5-diamino-6-methoxypyrimidin-4-yl carbonate

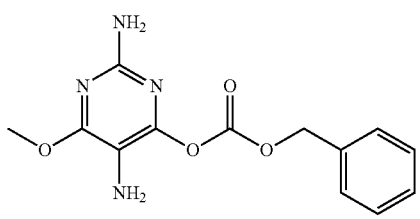 [SMILES: COc1nc(N)nc(OC(=O)OCc2ccccc2)c1N]

Benzyl 2,5-diamino-6-ethoxypyrimidin-4-yl carbonate

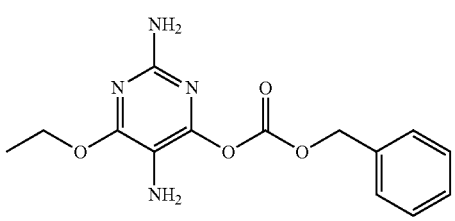 [SMILES: CCOc1nc(N)nc(OC(=O)OCc2ccccc2)c1N]

2,5-Diamino-6-ethoxypyrimidin-4-yl N-benzyl carbamate

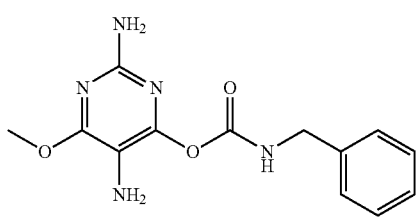 [SMILES: COc1nc(N)nc(OC(=O)NCc2ccccc2)c1N]

2,5-Diamino-6-ethoxypyrimidin-4-yl N-benzyl carbamate

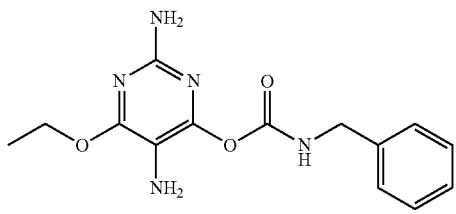 [SMILES: CCOc1nc(N)nc(OC(=O)NCc2ccccc2)c1N]

4-Methoxy-6-phenoxypyrimidine-2,5-diamine

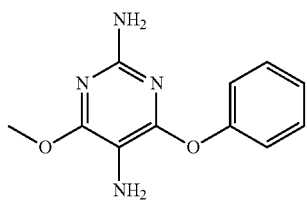 [SMILES: COc1nc(N)nc(Oc2ccccc2)c1N]

4-Ethoxy-6-phenoxypyrimidine-2,5-diamine

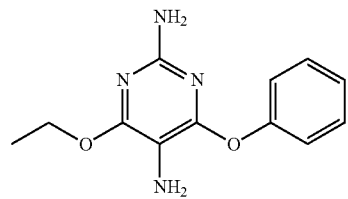 [SMILES: CCOc1nc(N)nc(Oc2ccccc2)c1N]

4-Propoxy-6-phenoxypyrimidine-2,5-diamine

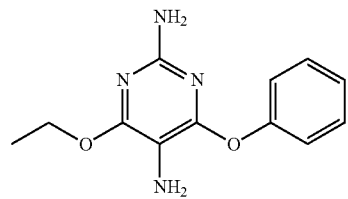 [SMILES: CCOc1nc(N)nc(Oc2ccccc2)c1N]

4-(2-Methylpropoxy)-6-phenoxypyrimidine-2,5-diamine

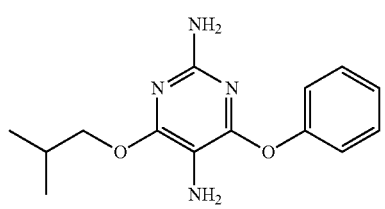 [SMILES: CC(C)COc1nc(N)nc(Oc2ccccc2)c1N]

4,6-Diphenoxypyrimidine-2,5-diamine

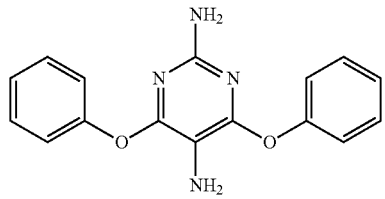 [SMILES: Nc1nc(Oc2ccccc2)c(N)c(Oc2ccccc2)n1]

4-Phenoxy-6-(prop-2-en-1-yloxy)pyrimidine-2,5-diamine

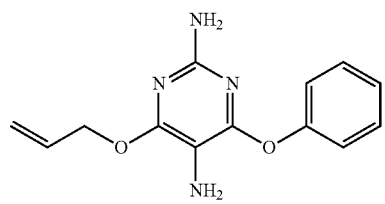 [SMILES: C=CCOc1nc(N)nc(Oc2ccccc2)c1N]

2,5-Diamino-6-methoxypyrimidin-4-yl benzoate

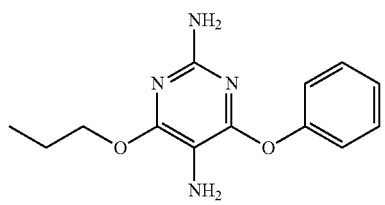

2,5-Diamino-6-ethoxypyrimidin-4-yl benzoate

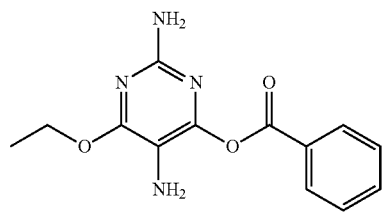 [SMILES: CCOc1nc(N)nc(OC(=O)c2ccccc2)c1N]

2,5-Diamino-6-propoxypyrimidin-4-yl benzoate

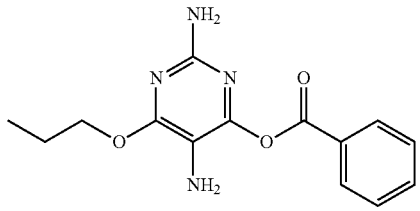

2,5-Diamino-6-(2-methylpropoxy)pyrimidin-4-yl benzoate

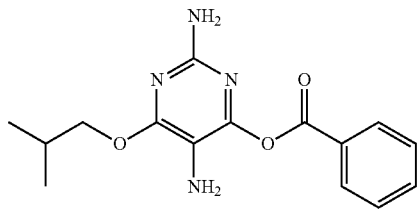 [SMILES: CCCOc1nc(N)nc(OC(=O)c2ccccc2)c1N]

2,5-Diamino-6-(benzoyloxy)pyrimidin-4-yl benzoate

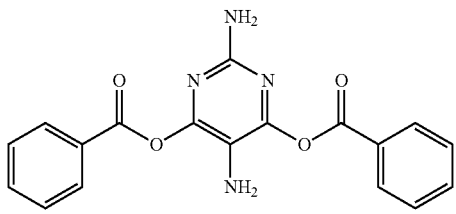 [SMILES: Nc1nc(OC(=O)c2ccccc2)c(N)c(OC(=O)c2ccccc2)n1]

2,5-Diamino-6-methoxypyrimidin-4-yl phenyl carbonate

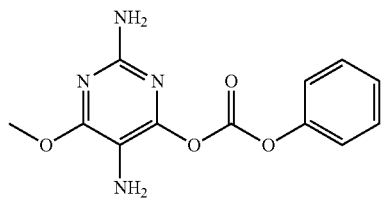 [SMILES: COc1nc(N)nc(OC(=O)Oc2ccccc2)c1N]

2,5-Diamino-6-ethoxypyrimidin-4-yl phenyl carbonate

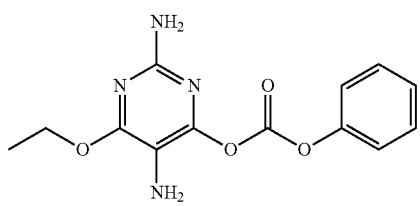 [SMILES: CCOc1nc(N)nc(OC(=O)Oc2ccccc2)c1N]

2,5-Diamino-6-methoxypyrimidin-4-yl N-phenylcarbamate

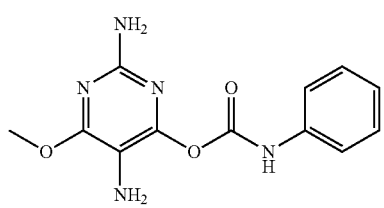

2,5-Diamino-6-ethoxypyrimidin-4-yl N-phenylcarbamate

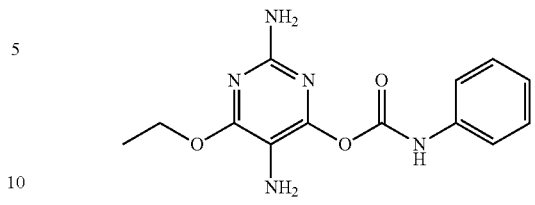

Some compounds within the above-mentioned group are extremely particularly preferred. A particularly preferred agent for oxidatively dyeing keratinic fibers is therefore further characterized in that it includes at least one compound of formula (I) that is selected from 4,6-dimethoxypyrimidine-2,5-diamine, 4-methoxy-6-ethoxypyrimidine-2,5-diamine, 4,6-diethoxypyrimidine-2,5-diamine, [(2,5-diamino-6-methoxypyrimidin-4-yl)oxy]methanol, [(2,5-diamino-6-ethoxypyrimidin-4-yl)oxy]methanol, [(2,5-diamino-6-methoxypyrimidin-4-yl)oxy]ethanol, [(2,5-diamino-6-ethoxypyrimidin-4-yl)oxy]ethanol, [(2,5-diamino-6-methoxypyrimidin-4-yl)oxy]methoxy)methanol, [(2,5-diamino-6-ethoxypyrimidin-4-yl)oxy]methoxy) methanol, 2-{2-[(2,5-diamino-6-methoxypyrimidin-4-yl)oxy]ethoxy}ethan-1-ol, 2-{2-[(2,5-diamino-6-ethoxypyrimidin-4-yl)oxy]ethoxy}ethan-1-ol, and/or the physiologically acceptable salts thereof.

The compounds of formula (I) according to the invention are amino compounds. These may also be used in the form of their physiologically acceptable salts, in particular the chlorides, sulfates, and bromides. Further preferred salts are derived from sulfonic acids, for example benzenesulfonates, p-toluene sulfone sulfonates, $C_1$-$C_4$ alkane sulfonates, or trifluoromethanesulfonates. Mono-, di-, tri-, tetra-, and higher adducts may be present as salts, depending on the number of amino groups included in the compounds according to the invention.

To be able to achieve a sufficiently high color intensity on the keratin fibers, it is preferred to use the compounds of formula (I) according to the invention in certain quantity ranges in the oxidative coloring agent.

An agent preferred according to the invention is characterized in that it includes one or more compounds of formula (I) in an overall quantity of 0.001 to 5.0% by weight, preferably 0.025 to 2.5% by weight, particularly preferably 0.05 to 2.0% by weight, and in particular preferably 0.1 to 1.5% by weight, in each case based on the total weight of the ready-to-apply agent.

All weight quantities mentioned above are based on the total weight of the ready-to-apply agent. The ready-to-apply agent is the agent which is ready for application, and which may be applied directly to the hair by the user or hairdresser. The agents according to the inventions are agents for oxidatively dyeing keratin fibers, and which require an oxidizing agent (preferably hydrogen peroxide) for forming the dyes. For stability reasons and for avoiding a premature dye-forming reaction, the agent which includes the oxidation dye precursors (M1), and the oxidizing agent (M2) are provided in separate containers. Both agents (M1) and (M2) are then mixed shortly before application, resulting in the ready-to-apply coloring agent. The content of the oxidation dyes in the ready-to-apply agent is relevant for the color intensity that is achievable on the keratin fibers. For this reason, all stated quantities which denote the content of the compounds of formula (I) must be based on the weight of the ready-to-apply agent.

In principle, the compounds of formula (I) may be included as the sole color-changing compounds in the agent according to the invention. However, the principle of the oxidative coloring is based on the oxidation dye precursors of the developer type not forming the actual dyes until the targeted coupling reaction with further oxidation dye precursors of the coupler type. Various shades may be achieved, depending on the coupler(s) used. It is therefore preferred according to the invention to use the compound(s) of formula (I) in combination with one or more oxidation dyes of the coupler type in the agent according to the invention.

Within the scope of the oxidative coloring, coupler components alone do not form significant coloration; rather, they always require the presence of developer components. Coupler components within the meaning of the invention allow at least one substitution of a chemical moiety of the coupler by the oxidized form of the developer component. In the process, covalent bonds form between the coupler component and the developer component.

At least one compound from one of the following classes is selected as a coupler component that is suitable according to the invention:
  m-aminophenol and/or derivatives thereof,
  m-diaminobenzene and/or derivatives thereof,
  o-diaminobenzene and/or derivatives thereof,
  o-aminophenol derivatives, for example o-aminophenol,
  naphthalene derivatives including at least one hydroxy group,
  di- or trihydroxybenzene and/or derivatives thereof,
  pyridine derivatives,
  pyrimidine derivatives that are different from formula (I) and are not tetra-substituted,
  monohydroxyindole derivatives and/or monoaminoindole derivatives,
  monohydroxyindoline derivatives and/or monoaminoindoline derivatives,
  pyrazolone derivatives, for example 1-phenyl-3-methylpyrazol-5-one,
  morpholine derivatives, for example 6-hydroxybenzomorpholine or 6-aminobenzomorpholine,
  quinoxaline derivatives, for example 6-methyl-1,2,3,4-tetrahydroquinoxaline.

Within the scope of this embodiment, mixtures of two or more compounds from one or more of these classes are likewise encompassed by the invention.

Suitable couplers may be selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methyl-phenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methyl-amino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, and/or 7-hydroxyindoline, and the physiologically acceptable salts thereof.

In this regard, it has been shown that the fastness properties of the resulting colorings may also be greatly influenced by the selection of specific developer/coupler combinations. For certain combinations of developers with particular couplers, the wash fastness and the light fastness are thus particularly good.

A very particularly preferred agent is therefore characterized in that it additionally includes at least one oxidation dye precursor of the coupler type from the group consisting of 3-aminophenol, 5-amino-2-methylphenol, 3-amino-2-chloro-6-methylphenol, 2-(2,4-diaminophenoxy)ethanol, 1,3-bis-(2,4-diaminophenoxy)propane, 1-methoxy-2-amino-4-(2-hydroxyethylamino)benzene, 2,7-dihydroxynaphthalene, 1,5-dihydroxynaphthalene, 1-naphthol, resorcinol, 2-methylresorcinol, 4-chlororesorcinol, 2-amino-3-hydroxypyridine, 3-amino-6-methoxy-2-methylaminopyridine, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-2-methylphenyl}amino)ethanol, 2,6-dihydroxy-3,4-dimethylpyridine, 1-methyl-2,6-bis(2-hydroxyethylamino)benzene, and/or a physiologically acceptable salt of these compounds.

For the development of a marketable shade which meets all application-related requirements, in most cases it is usually not sufficient to use one developer in combination with one coupler. In particular for fine adjustment of the color, dye combinations with multiple oxidation dye precursors are used in the marketed products.

In the development of shadings using the compounds of formula (I) according to the invention, it has been found that certain combinations of the developer of formula (I)/coupler 1/coupler 2 result in colorings having particularly outstanding intensities and fastness properties.

A very particularly preferred agent is therefore characterized in that it additionally includes
  one or more oxidation dye precursors of the coupler type from the group consisting of resorcinol, 2-methylresorcinol, and/or 4-chlororesorcinol and
  one or more oxidation dye precursors of the coupler type from the group consisting of (2,4-diaminophenoxy)ethanol, 1,3-bis(2,4-diaminophenoxy)propane, 1-methoxy-2-amino-4-(2-hydroxyethylamino)benzene.

A very particularly preferred agent is therefore further characterized in that it additionally includes
  one or more oxidation dye precursors of the coupler type from the group consisting of resorcinol, 2-methylresorcinol, and/or 4-chlororesorcinol and
  one or more oxidation dye precursors of the coupler type from the group consisting of 2-amino-3-hydroxypyridine, 3-amino-6-methoxy-2-methylaminopyridine, and/or 2,6-dihydroxy-3,4-dimethylpyridine.

A very particularly preferred agent is therefore further characterized in that it additionally includes
  one or more oxidation dye precursors of the coupler type from the group consisting of resorcinol, 2-methylresorcinol, and/or 4-chlororesorcinol and one or more oxidation dye precursors of the coupler type from the group consisting of 1-naphthol, 1,5-dihydroxynaphthalene, and/or 1-methyl-2,6-bis(2-hydroxyethylamino)benzene.

The coupler components are preferably used in an overall quantity of 0.0001 to 10% by weight, preferably 0.01 to 5.0% by weight, in each case based on the ready-to-apply agent. In addition to the compound(s) of formula (I), the agent according to the invention may include even further oxidation dye precursors of the developer type.

Preferred further developer components are selected from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds. Particularly preferred additional developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof.

A particularly preferred agent is therefore further characterized in that it additionally includes at least one oxidation dye precursor of the developer type from the group consisting of:
p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N-bis-(2-hydroxyethyl)-N,N-bis-(4-aminophenyl)-1,3-diaminopropan-2-ol, bis-(2-hydroxy-5-aminophenyl)methane, 1,3-bis-(2,5-diaminophenoxy)propan-2-ol, N,N-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl) phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine benzene, and/or a physiologically acceptable salt of these compounds.

Within the group of developers which are additionally usable in the agent, selected compounds have particularly good compatibility with the compounds of formula (I). These are the oxidation dyes of the developer type, which are selected from the group consisting of 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl) methane, 4,5-diamino-1-(2-hydroxyethyl)pyrazole, and/or a physiologically acceptable salt thereof. Use of these combinations offers the advantage that the corresponding coloring agents cause hardly any skin irritation, and no shifts in the shading occur on keratin fibers.

A very particularly preferred agent is therefore further characterized in that it additionally includes at least one oxidation dye precursor of the developer type from the group consisting of 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 4,5-diamino-1-(2-hydroxyethyl)pyrazole, and/or a physiologically acceptable salt of these compounds.

The additional developer components are preferably used in an overall quantity of 0.0001 to 10% by weight, preferably 0.001 to 5% by weight, in each case based on the ready-to-apply agent.

In addition, the agents according to the invention may include at least one direct dye. Direct dyes are dyes which are directly absorbed into the hair and which require no oxidative process for forming the color. Direct dyes are typically nitrophenylenediamines, nitroaminophenols, azo dyes, anthraquinones, triarylmethane dyes, or indophenols.

The direct dyes may be used in an overall quantity of 0.001 to 20% by weight, in particular 0.05 to 5% by weight, in each case based on the weight of the ready-to-apply agent. The overall quantity of direct dyes in the ready-to-apply agent is preferably no more than 3% by weight.

Direct dyes may be subdivided into anionic, cationic, and nonionic direct dyes, which are selected and used by those skilled in the art depending on the requirements of the carrier base.

Preferred anionic direct dyes are the compounds known by the international designations or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

In particular, nonionic nitro dyes, quinone dyes, and neutral azo dyes are suited as nonionic direct dyes. Preferred nonionic direct dyes are the compounds HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino 4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-4-nitrophenol.

The agents according to the invention may also include dyes analogous to nature in addition to the compound according to formula (I). Compositions according to the invention which include the precursors of dyes analogous to nature are preferably used as air oxidative coloring agents.

As a result, in this embodiment the stated compositions are not combined with an additional oxidizing agent.

Particularly well suited as precursors of hair dyes analogous to nature are derivatives of 5,6-dihydroxyindoline, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, and 5,6-dihydroxyindoline-2-carboxylic acid, in addition to derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, and physiologically acceptable salts of the above-mentioned compounds.

The dye precursors of dyes analogous to nature are in each case preferably used in a quantity of 0.001 to 5% by weight, based on the weight of the ready-to-apply agent.

The dye formation is initiated by the presence of an oxidizing agent; at the same time, the oxidizing agent also oxidatively destroys the hair's own dyes (melanins), thus causing lightening of the original hair color. The concentration of oxidizing agent used is selected as a function of the lightening effect that is desired in addition to the coloring of the keratin fibers. Persulfates, peroxodisulfates, chlorites, hypochlorites, and in particular hydrogen peroxide and/or one of its solid addition products with organic or inorganic compounds are suitable as oxidizing agent.

To prevent a premature undesirable reaction of the oxidation dye precursors due to the oxidizing agent, oxidation dye precursors and the oxidizing agents themselves are advantageously packaged separately, and not brought into contact until just before use. For the user of the oxidative coloring agent, it is particularly convenient and therefore preferred to use the agents provided in a corresponding multicomponent packaging unit (kit-of-parts).

A second subject matter of the present invention relates to a multicomponent packaging unit (kit-of-parts) for oxidatively dyeing keratinic fibers, comprising two agents (M1) and (M2) that are separately packaged, wherein
  agent (M1) is an agent of the first subject matter of the invention,
  agent (M2) includes an oxidizing agent in an aqueous cosmetic carrier.

The oxidizing agent preparation (i.e., agent (M2)) preferably includes hydrogen peroxide and/or one of its solid addition products with organic or inorganic compounds, such as urea, melamine, and sodium borate, as oxidizing agent.

The quantity of oxidizing agent in the ready-to-apply agent (i.e., in the mixture of (M1) and (M2)) is preferably 0.5 to 12% by weight, preferably 0.5 to 6% by weight, more preferably 1.0 to 5.0% by weight, even more preferably 1.5 to 4.0% by weight, and particularly preferably 1.5 to 3.0% by weight, based on the total weight of the mixture of (M1) and (M2).

Therefore, a multicomponent packaging unit (kit-of-parts) for oxidatively dyeing keratinic fibers, comprising two separately packaged agents (M1) and (M2), is preferred, wherein
  agent (M1) is an agent of the first subject matter of the invention,
  agent (M2) includes hydrogen peroxide in an aqueous cosmetic carrier, and
  the mixture of (M1) and (M2) includes hydrogen peroxide in a quantity of 0.5 to 6.0% by weight, preferably 1.0 to 5.0% by weight, more preferably 1.5 to 4.0% by weight, and particularly preferably 1.5 to 3.0% by weight, based on the total weight of the mixture of (M1) and (M2).

However, according to the invention the oxidation dye may also be applied to the hair together with a catalyst which activates the oxidation of the dye precursors. Such catalysts are certain enzymes, iodides, quinones, or metal ions, for example.

In addition, it has been found to be advantageous when the oxidizing agent preparations include at least one stabilizer or complexing agent. Examples of common complexing agents and stabilizers that are preferred within the scope of the present invention are polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserinediacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylenediamine-N,N'-diglutaric acid (EDDG), 2-hydroxypropylenediamine-N,N'-disuccinic acid (HPDDS), diaminoalkyldi-(sulfosuccinic acid) (DDS), ethylenedicysteic acid (EDC), ethylenediamine-N,N'-bis(ortho-hydroxyphenyl) acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, and the salts and/or derivatives thereof, geminal diphosphonic acids such as 1-hydroxyethane-1,1-diphosphonic acid (HEDP), the higher homologues thereof including up to 8 carbon atoms, derivatives thereof including hydroxy or amino groups, and 1-aminoethane-1,1-diphosphonic acid, the higher homologues thereof including up to 8 carbon atoms, derivatives thereof including hydroxy or amino groups, and aminophosphonic acids such as ethylenediamine tetra(methylenephosphonic acid) (EDTMP), diethylenetriamine penta(methylenephosphonic acid) (DTPMP) and the higher homologues thereof, or nitrilotri(methylenephosphonic acid), phosphonopolycarboxylic acids such as 2-phosphonobutane-1,2,4-tricarboxylic acid, cyclodextrins, and alkali stannates (sodium stannate), alkali pyrophosphates (tetrasodium pyrophosphate, disodium pyrophosphate), alkali phosphates (sodium phosphate), and phosphoric acid and the salts thereof.

For sufficient swelling of the keratin fibers, the ready-to-apply oxidative coloring agent is preferably set to an alkaline pH. The dyeing processes on keratin fibers also customarily proceed in an alkaline environment. However, to protect the keratin fibers and also the skin to the greatest extent possible, setting a pH that is too high is not desirable. It is therefore preferred when the pH of the ready-to-apply agent has a value of 7.0 to 10.5, preferably 7.5 to 9.5, more preferably 8.0 to 9.0.

The water content in the application mixture is preferably a quantity of at least 50% by weight, preferably at least 60% by weight, more preferably at least 70% by weight, and particularly preferably at least 80% by weight, based on the total weight of the mixture of (M1) and (M2).

A particularly preferred multicomponent packaging unit (kit-of-parts) for oxidatively dyeing keratinic fibers is further characterized in that the mixture of (M1) and (M2) includes water in a quantity of at least 50% by weight, preferably at least 60% by weight, more preferably at least 70% by weight, and particularly preferably at least 80% by weight, based on the total weight of the mixture of (M1) and (M2), and the mixture of (M1) and (M2) has a pH of 7.0 to 10.5, preferably 7.5 to 9.5, more preferably 8.0 to 9.0.

The stated pH values are values that have been measured at a temperature of 22° C. with a glass electrode. The pH may be measured using a standard glass electrode; glass electrodes are often designed as combination electrodes.

The alkalizing agents that are usable according to the invention for setting the preferred pH may be selected from ammonia, alkanolamines, basic amino acids, and inorganic alkalizing agents such as (earth) alkaline metal hydroxides, (earth) alkaline metal metasilicates, (earth) alkaline metal phosphates, and (earth) alkaline metal hydrogen phosphates. Preferred inorganic alkalizing agents are sodium hydroxide, potassium hydroxide, sodium silicate, and sodium metasilicate. Organic alkalizing agents that are usable according to the invention are preferably selected from monoethanolamine, 2-amino-2-methylpropanol, and triethanolamine. The basic amino acids that are usable as alkalizing agents according to the invention are preferably selected from the group consisting of arginine, lysine, ornithine, and histidine, particularly preferably arginine. However, in the testing for the present invention, it has been found that further agents preferred according to the invention are characterized in that they additionally include an organic alkalizing agent. One embodiment of the first subject matter of the invention is characterized in that the agent additionally includes at least one alkalizing agent that is selected from the group consisting of ammonia, alkanolamines, and basic amino acids, in particular ammonia, monoethanolamine, and arginine or the acceptable salts thereof. The alkalizing agent(s) together with the oxidation dye precursors are preferably provided in color preparation (M1).

The oxidative color change agents (i.e., color preparation (M1) and/or the oxidizing agent preparation (i.e., agent (M2)) may also include further active substances, auxiliary substances, and additives in order to improve the coloring or lightening power and to set further desired properties in the agent.

The ready-to-apply coloring agents are preferably provided as a liquid preparation, and optionally a further surface-active substance is additionally added to the agents; depending on the field of application, such surface-active substances are referred to as surfactants or as emulsifiers. They are preferably selected from anionic, zwitterionic, amphoteric, and nonionic surfactants and emulsifiers.

Agents which are suitable according to the invention are characterized in that the agent additionally includes at least one anionic surfactant. Preferred anionic surfactants are fatty acids, alkyl sulfates, alkyl ether sulfates, and ether carboxylic acids including 10 to 20 C atoms in the alkyl group and up to 16 glycol ether groups in the molecule.

Agents which are suitable according to the invention are characterized in that the agent additionally includes at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl imidazolines. One preferred zwitterionic surfactant is known by the INCI name Cocamidopropyl betaine.

Agents which are suitable according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred amphoteric surfactants are N-cocoalkylamino propionate, cocoacylaminoethylamino propionate, and $C_{12}$-$C_{18}$ acyl sarcosine.

In addition, it has proven to be advantageous when the agents include further, noniogenic surface-active substances. Preferred nonionic surfactants are alkyl polyglycosides and alkylene oxide addition products with fatty alcohols and fatty acids in each case including 2 to 30 mol ethylene oxide per mol fatty alcohol or fatty acid. Preparations having excellent properties are likewise obtained when they include fatty acid esters of ethoxylated glycerin as nonionic surfactants.

The nonionic, zwitterionic, or amphoteric surfactants are used in proportions of 0.1 to 45% by weight, preferably 1 to 30% by weight, and very particularly preferably 1 to 15% by weight, based on the total quantity of the ready-to-apply agents.

The ready-to-apply color-changing agents may also include at least one thickener. In principle, there are no limitations with regard to these thickeners. Organic as well as strictly inorganic thickeners may be used.

Suitable thickeners are anionic synthetic polymers, cationic synthetic polymers, naturally occurring thickeners, such as nonionic guar gums, scleroglucan gums, or xanthan gums, gum arabic, gum ghatti, karaya gum, gum tragacanth, carrageenan gum, agar-agar, locust bean gum, pectins, alginates, starch fractions, and derivatives such as amylose, amylopectin, and dextrins, and cellulose derivatives such as methylcellulose, carboxyalkyl celluloses, and hydroxyalkyl celluloses, nonionic synthetic polymers such as polyvinyl alcohol or polyvinylpyrrolidinone, and inorganic thickeners, in particular phyllosilicates such as bentonite, in particular smectites such as montmorillonite or hectorite.

Furthermore, it has proven to be advantageous when the coloring agents, in particular when they additionally include hydrogen peroxide, include at least one stabilizer or complexing agent. Particularly preferred stabilizers are phenacetin, alkali benzoates (sodium benzoate), and salicylic acid. In addition, all complexing agents of the prior art may be used. Complexing agents preferred according to the invention are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

In addition, the agents according to the invention may include further active substances, auxiliary substances, and additives, for example nonionic polymers such as vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or nonvolatile, straight-chain, branched, or cyclic, crosslinked or noncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane (A)-polyoxyalkylene (B) block copolymers, grafted silicone polymers; cationic polymers such as quaternized cellulose ethers, polysiloxanes having quaternary groups, dimethyldiallyl ammonium chloride polymers, acrylamide dimethyldiallyl ammonium chloride copolymers, dimethylaminoethyl methacrylate-vinylpyrrolidinone copolymers quaternized with diethyl sulfate, vinylpyrrolidinone-imidazolinium methochloride copolymers, and quaternized polyvinyl alcohol; zwitterionic and amphoteric polymers; anionic polymers, for example polyacrylic acids or cross-linked polyacrylic acids; structurizers such as glucose, maleic acid, and lactic acid, hair conditioning compounds such as phospholipids, for example lecithin and cephalins; fragrance oils, dimethyl isosorbide, and cyclodextrins; fiber structure-improving active substances, in particular mono-, di-, and oligosaccharides such as glucose, galactose, fructose, fruit sugar, and lactose; dyes for coloring the agent; anti-dandruff active substances such as piroctone olamine, zinc omadine, and climbazole; amino acids and oligopeptides; animal- and/or plant-based protein hydrolysates, and in the form of their fatty acid condensation products or optionally anionically or cationically modified derivatives; plant oils; light protection agents and UV blockers; active substances such as panthenol, pantothenic acid, pantolactone, allantoin, pyrrolidinone carboxylic acids and the salts thereof, and bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling agents and penetration agents such as glycerin, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescence agents such as ethylene glycol mono- and distearate and PEG-3-distearate; pigments, and propellants such as propane-butane mixtures, $N_2O$, dimethyl ether, $CO_2$, and air.

Those skilled in the art will select these further substances according to the desired properties of the agents. With regard to further optional components and the quantities of these components used, explicit reference is made to relevant handbooks known to those skilled in the art. The additional active substances and auxiliary substances are preferably used in the agents according to the invention in each case in quantities of 0.0001 to 25% by weight, in particular 0.0005 to 15% by weight, in each case based on the total weight of the color preparation (M1) and/or the oxidizing agent preparation (M2).

The agents according to the invention show extremely good suitably for dyeing keratinic fibers; the dyed fibers have very good wash fastness, very good light fastness, and very good leveling properties.

A further subject matter of the present invention therefore relates to the use of an agent of the first subject matter of the invention for obtaining colorings having improved leveling properties, increased light fastness, and improved wash fastness.

The multicomponent packaging units (kits-of-parts) also show very good suitability for achieving colorings having very good wash fastness, good light fastness, and good leveling properties.

A further subject matter of the present invention relates to the use of an agent of the second subject matter of the invention for obtaining colorings having improved leveling properties, increased light fastness, and improved wash fastness.

The statements concerning the agents according to the invention apply mutatis mutandis with regard to further preferred embodiments of the multicomponent packaging units (kits-of-parts) according to the invention and the uses according to the invention.

EXAMPLES

Synthesis Examples

Synthesis Example 1

Synthesis of 4,6-dimethoxypyrimidine-2,5-diamine dihydrochloride (E1)

1.1. Synthesis of 2-amino-4,6-dimethoxypyrimidine

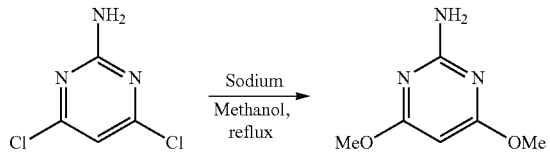 [SMILES: Nc1nc(Cl)cc(Cl)n1 ; COc1cc(OC)nc(N)n1]

32.8 g (0.200 mol) of 2-amino 4,6-dichloropyrimidine was added to a solution of 15.0 g (0.652 mol) sodium in 400 mL methanol and heated under reflux for 13 hours, with stirring. Stirring was then performed for an additional 3 days at room temperature. After the reaction was complete, the precipitated sodium chloride was removed by filtration and the solution was concentrated to dryness. The residue was washed with 500 mL water. After drying, 2-amino 4,6-dimethoxypyrimidine (26.5 g, 85%) was obtained as a pale yellow solid.

Mp.: 96-101° C.
$^1$H NMR (300 MHz, $d_6$-DMSO): δ=3.80 (s, 6 H, 4-OMe, 6-OMe), 5.38 (s, 1 H, 5-H), 6.59 (s, 2 H, $NH_2$)
$^{13}$C NMR (125 MHz, $d_6$-DMSO): δ=53.2 (4-OMe, 6-OMe), 77.9 (5-C), 162.8 (2-C), 171.7 (6-C, 4-C)

1.2. Synthesis of 2-amino-4,6-dimethoxy-5-nitrosopyrimidine

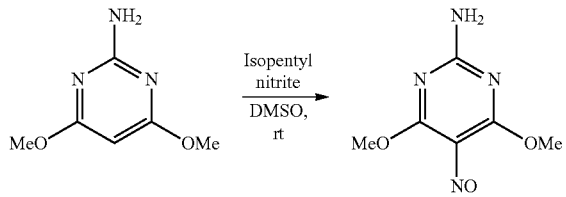

34.8 g (0.297 mol) of isopentyl nitrite was added to a solution of 41.9 g (0.270 mol) 2-amino-4,6-dimethoxypyrimidine in 675 mL dimethylsulfoxide and stirred for 96 hours at room temperature. After the reaction was complete, the deep blue solution was poured into 2.5 L water and stirred for 1 hour at room temperature. The resulting precipitate was filtered off and washed with water. After drying, 2-amino-4,6-dimethoxy-5-nitrosopyrimidine (32.8 g, 66%) was obtained as a light blue solid.

Mp.: 215-218° C. (decomposition)
$^1$H NMR (300 MHz, $d_6$-DMSO): δ=3.94 (s, 6 H, 4-OMe, 6-OMe), 8.28 (s, 2 H, $NH_2$).

$^{13}$C NMR (125 MHz, d$_6$-DMSO): δ=54.9 (4-OMe, 6-OMe), 141.9 (5-C), 163.3 (6-C, 4-C), 173-0 (2-C)

1.3. Synthesis of 4,6-dimethoxypyrimidine-2,5-diamine dihydrochloride (E1)

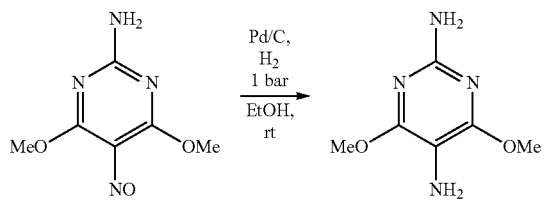

0.5 g (5%) palladium on carbon was added to a solution of 7.37 g (0.04 mol) 2-amino 4,6-dimethoxypyrimidine in 400 mL ethanol and agitated for 17 hours at room temperature under a hydrogen pressure of 1 bar. After the reaction was complete, the reaction solution was poured into 60 mL hydrochloric acid (10% in water). The catalyst was filtered off. The filtrate was concentrated to completion on a rotary evaporator. The residue was stirred into a small amount of ice cold ethanol, resulting in a precipitate which was filtered off and washed with a small amount of ice cold ethanol. After drying, 4,6-dimethoxypyrimidine-2,5-diamine dihydrochloride (4.15 g, 50%) was obtained as a light beige solid.

$^1$H NMR (300 MHz, d$_6$-DMSO): δ=3.98 (s, 6 H, 4-OMe, 6-OMe), 4.85 (brs, 4 H, NH$_2$)

$^{13}$C NMR (125 MHz, d$_6$-DMSO): δ=58.0 (4-OMe, 6-OMe), 91.2 (5-C), 157.4 (2-C), 163.7 (4-C), 168.1 (6-C)

Synthesis Example 2

Synthesis of 4,6-diethoxypyrimidine-2,5-diamine dihydrochloride (E2)

2.1. Synthesis of 2-amino 4,6-diethoxypyrimidine

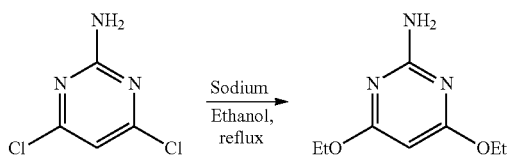 [SMILES: Nc1nc(Cl)cc(Cl)n1 ; CCOc1cc(OCC)nc(N)n1]

A suspension of 32.8 g (0.200 mol) 2-amino-4,6-dichloropyrimidine in 1.5 L ethanol was added to a solution of 15.3 g (0.670 mol) sodium in 600 mL ethanol and heated under reflux for 6.5 hours, with stirring, and then stirred for 17 hours at 70° C. After the reaction was complete, the precipitated NaCl was removed by filtration and the filtrate was concentrated to completion on a rotary evaporator. The residue was washed with 500 mL water. After drying, 2-amino-4,6-diethoxypyrimidine (35.7 g, 97%) was obtained as a pale yellow solid.

Mp.: 100-103° C.

$^1$H NMR (300 MHz, d$_6$-DMSO): δ=1.21 (t, 6 H, CH$_3$), 4.21 (q, 4 H, CH$_2$), 5.30 (s, 1 H, 5-H), 6.49 (s, 2 H, NH$_2$)

$^{13}$C NMR (125 MHz, d$_6$-DMSO): δ=14.5 (CH$_3$), 61.1 (—O—CH$_2$—), 78.3 (5-C), 162.8 (2-C), 171.2 (6-C, 4-C)

2.2. Synthesis of 2-amino-4,6-diethoxy-5-nitrosopyrimidine

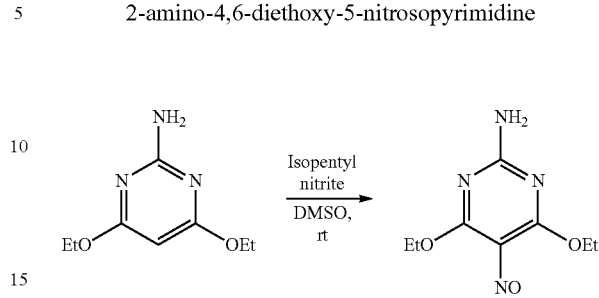

24.6 g (0.21 mol) of isopentyl nitrite was added to a solution of 34.8 g (0.19 mol) 2-amino-4,6-diethoxypyrimidine in 475 mL dimethylsulfoxide and stirred for 119 hours at room temperature. After the reaction was complete, the deep blue solution was poured into 1.9 L water and stirred for 1 hour at room temperature, and the resulting precipitate was filtered off. The residue was washed with water. The solid that was obtained was recrystallized twice from ethyl acetate (600 mL and 300 mL). After drying, 2-amino-4,6-diethoxy-5-nitrosopyrimidine (10.8 g, 27%) was obtained as a dark blue solid.

Mp.: 215–218° C. (decomposition)

$^1$H NMR (300 MHz, d$_6$-DMSO): δ=1.38 (t, 6 H, CH$_3$), 4.47 (q, 4 H, CH$_2$), 8.21 (s, 2 H, NH$_2$)

$^{13}$C NMR (125 MHz, d$_6$-DMSO): δ=14.3 (CH$_3$), 62.9 (—O—CH$_2$—), 141.4 (5-C), 163.0 (6-C, 4-C), 170.4 (2-C)

2.3. Synthesis of 4,6-diethoxypyrimidine-2,5-diamine dihydrochloride (E2)

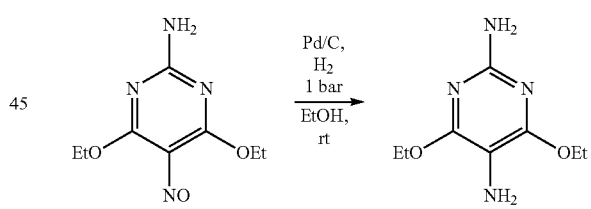

1.0 g (5%) palladium on carbon was added to a solution of 14.1 g (0.066 mol) 2-amino-4,6-diethoxy-5-nitrosopyrimidine in 400 mL ethanol and agitated for 21 hours at room temperature under a hydrogen pressure of 1 bar. After the reaction was complete, the reaction solution was poured into 100 mL hydrochloric acid (10% in water), filtered from the catalyst, and concentrated to dryness. The yellow oil that was obtained was combined with ethanol and re-concentrated. The resulting precipitate was suctioned off and washed with a small amount of ice cold ethanol. After drying, 4,6-diethoxypyrimidine-2,5-diamine dihydrochloride (10.9 g, 61%) was obtained as a light yellow solid.

$^1$H NMR (300 MHz, d$_6$-DMSO): δ=1.26 (t, 6 H, CH$_3$), 4.31 (q, 4 H, CH$_2$), 6.70 (brs, 4 H, NH$_2$).

$^{13}$C NMR (125 MHz, d$_6$-DMSO): δ=14.8 (CH$_3$), 62.9 (—O—CH$_2$—), 87.0 (5-C), 161.1 (2-C), 163.8 (6-C, 4-C).

2. Color Examples

2.1. Production of the Color Creams

The following color creams were produced:

| | |
|---|---|
| Hydrenol ® D[1] | 8.5% by weight |
| Lorol ® technical[2] | 2.0% by weight |
| Texapon ® NSO[3] | 20.0% by weight |
| Dehyton ® K[4] | 12.5% by weight |
| Eumulgin ® B2[5] | 0.75% by weight |
| Sodium sulfite | 1.0% by weight |
| Ammonium sulfate | 1.0% by weight |
| Developer component | 3 mmol |
| Coupler component | 3 mmol |
| Water | ad 100 |

[1] $C_{16-18}$ fatty alcohol (INCI name: Cetearyl Alcohol) (Cognis)
[2] $C_{12-18}$ fatty alcohol (INCI name: Coconut Alcohol) (Cognis)
[3] Lauryl ether sulfate, sodium salt (approximately 27.5% active substance; INCI name: Sodium Laureth Sulfate) (Cognis)
[4] N,N-Dimethyl-N-($C_{8-18}$ cocoamidopropyl)ammonium acetobetaine (approximately 30% active substance; INCI name: Aqua (water), Cocoamidopropyl Betaine) (Cognis)
[5] Cetylstearyl alcohol with approximately 20 EG units (INCI name: Ceteareth-20) (Cognis)

Hydrenol D and Lorol technical were melted together with Texapon NSO, Dehyton K, and Eumulgin B2 at 80° C. The melt was then emulsified with the sodium sulfite and ammonium sulfate dissolved in a portion of the water. The developer according to the invention was dissolved in another portion of the stated quantity of water, with heating, and added thereto with stirring. The coupler was likewise dissolved in a portion of the stated quantity of water and added thereto with stirring. The formulation was then filled with water to 100% and stirred cold.

The color cream obtained in this way was mixed in a 1:1 ratio with the following developer dispersion, having a hydrogen peroxide content of 6%.

| | |
|---|---|
| Dipicolinic acid | 0.1% by weight |
| Sodium pyrophosphate | 0.03% by weight |
| Turpinal ® SL[6] | 1.50% by weight |
| Texapon ® N28[7] | 2.00% by weight |
| Acrysol ® 22[8] | 0.60% by weight |
| Hydrogen peroxide, 50% | 6.00% by weight |
| Sodium hydroxide solution, 45% | 0.80% by weight |
| Water | ad 100% by weight |

[6] 1-Hydroxyethane-1,1-diphosphonic acid (approximately 58-61% active substance content; INCI name: Etidronic Acid, Aqua (water)) (Solutia)
[7] Lauryl ether sulfate sodium salt (at least 26.5% active substance content; INCI name: Sodium Laureth Sulfate) (Cognis)
[8] Acrylic polymer (approximately 29.5-30.5% solids in water; INCI name: Acrylates/Steareth-20 Methacrylate Copolymer)

For the coloring process, a 4-fold quantity of the ready-to-apply mixture was applied in each case to a strand of 80% grayed hair (Kerling). After an exposure time of 30 minutes at 32° C., the strands were rinsed off and thoroughly washed with a customary hair washing agent. After drying, the coloring of the strands was visually assessed under a daylight lamp. The color results are summarized in the following table.

TABLE 1

Colorings with 4,6-dimethoxypyrimidine-2,5-diamine dihydrochloride (E1)

| Example | Coupler component | Obtained shading/color intensity |
|---|---|---|
| 1 | Resorcinol | Grayish red (+++) |
| 2 | 3-Amino 2-methylamino-6-methoxypyridine | Sepia (+++) |
| 3 | 5-Amino 2-methylphenol | Grayish magenta (++) |
| 4 | 3-Amino-2-hydroxypyridine | Redhead (+) |
| 5 | 1,3-bis(2,4-diaminophenoxy)propane | Dark magenta (+++) |
| 6 | 1-Naphthol | Matte violet (++) |
| 7 | 2-Methylresorcinol | Brownish-red (+++) |
| 8 | 1,5-Dihydroxynaphthalene | Grayish ruby (++) |
| 9 | 1-Methyl-2,6-bis-(2-hydroxyethylamino) benzene | Madder red (+++) |

(+++) High intensity
(++) Medium intensity
(+) Low intensity

TABLE 2

Colorings with 4,6-dimethoxypyrimidine-2,5-diamine dihydrochloride (E2)

| Example | Coupler component | Obtained shading/color intensity |
|---|---|---|
| 1 | Resorcinol | Grayish red (+++) |
| 2 | 3-Amino 2-methylamino-6-methoxypyridine | Dark brown (+++) |
| 3 | 5-Amino 2-methylphenol | Rosewood (++) |
| 4 | 3-Amino-2-hydroxypyridine | Sahara red (++) |
| 5 | 1,3-bis(2,4-diaminophenoxy)propane | Dark purple (+++) |
| 6 | 1-Naphthol | Matte violet (++) |
| 7 | 2-Methylresorcinol | Grayish red (+++) |
| 8 | 1,5-Dihydroxynaphthalene | Purplish-gray (+++) |
| 9 | 1-Methyl-2,6-bis-(2-hydroxyethylamino) benzene | Cerise (+++) |

(+++) High intensity
(++) Medium intensity
(+) Low intensity

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for oxidatively dyeing keratinic fibers, including in a cosmetic carrier at least one compound of formula (I) as an oxidation dye precursor of the developer type:

(I)

[Chemical structure: pyrimidine ring with Y at position 2, $R_1$–O– at position 4, $R_2$–O– at position 6, and $NH_2$ at position 5]

in which

R$^1$, R$^2$ independently are a hydrogen atom, a C$_1$-C$_6$ alkyl group, a C$_2$-C$_6$ alkenyl group, a hydroxy-C$_1$-C$_6$ alkyl group, a polyhydroxy-C$_2$-C$_6$ alkyl group, a C$_1$-C$_6$ alkoxy-C$_1$-C$_6$ alkyl group, a hydroxy-C$_1$-C$_6$ alkyoxy-C$_1$-C$_6$ alkyl group, a C$_1$-C$_6$ alkoxy-C$_1$-C$_6$ alkyl group, a carboxy-C$_1$-C$_6$ alkyl group, a C$_1$-C$_6$ alkanoyl group, a C$_1$-C$_6$ alkoxycarbonyl group, a C$_1$-C$_6$ alkylaminocarbonyl group, a (di-C$_1$-C$_6$ alkylamino)carbonyl group, an aryl group, a heteroaryl group, or a (R$^3$R$^4$N)—C$_2$-C$_6$ alkyl group, wherein R$^3$, R$^4$ independently are a hydrogen atom, a C$_1$-C$_6$ alkyl group, a hydroxy-C$_1$-C$_6$ alkyl group, an amino-C$_1$-C$_6$ alkyl group, a C$_1$-C$_6$ alkoxy-C$_1$-C$_6$ alkyl group, an aryl group, or a heteroaryl group, and Y is a hydroxy group, an amino group, or a C$_1$-C$_6$ alkylamino group, with the condition that at least one of the moieties from the group R$^1$ and R$^2$ does not stand for a hydrogen atom, or the physiologically acceptable salt thereof, wherein the one or more compounds of formula (I) are included in an overall quantity of 0.001 to 5.0% by weight based on the total weight of a ready-to-apply agent.

2. The agent according to claim 1, wherein R$^1$ and R$^2$ independently are a C$_1$-C$_6$ alkyl group, a hydroxy C$_1$-C$_6$ alkyl group, a C$_1$-C$_6$ alkoxy-C$_1$-C$_6$ alkyl group, a C$_1$-C$_6$ alkanoyl group, a C$_1$-C$_6$ alkoxycarbonyl group, or an aryl group.

3. The agent according to claim 1, wherein Y stands for a hydroxy group or for an amino group.

4. The agent according to claim 1, wherein R$^1$ and R$^2$ both stand for a methyl group and Y stands for an amino group.

5. The agent according to claim 1, wherein the at least one compound of formula (I) is selected from the group consisting of 4,6-dimethoxypyrimidine-2,5-diamine, 4-methoxy-6-ethoxypyrimidine-2,5-diamine, 4,6-diethoxypyrimidine-2,5-diamine, [(2,5-diamino-6-methoxypyrimidin-4-yl)oxy]methanol, [(2,5-diamino-6-ethoxypyrimidin-4-yl)oxy]methanol, [(2,5-diamino-6-methoxypyrimidin-4-yl)oxy]ethanol, [(2,5-diamino-6-ethoxypyrimidin-4-yl)oxy]ethanol, [(2,5-diamino-6-methoxypyrimidin-4-yl)oxy]methoxy)methanol, [(2,5-diamino-6-ethoxypyrimidin-4-yl)oxy]methoxy)methanol, 2-{2-[(2,5-diamino-6-methoxypyrimidin-4-yl)oxy]ethoxy}ethan-1-ol, 2-{2-[(2,5-diamino-6-ethoxypyrimidin-4-yl)oxy]ethoxy}ethan-1-ol, and the physiologically acceptable salts thereof.

6. The agent according to claim 1, further including at least one oxidation dye precursor of the coupler type selected from the group consisting of 3-aminophenol, 5-amino-2-methylphenol, 3-amino-2-chloro-6-methylphenol, 2-(2,4-diaminophenoxy)ethanol, 1,3-bis-(2,4-diaminophenoxy)propane, 1-methoxy-2-amino-4-(2-hydroxyethylamino)benzene, 2,7-dihydroxynaphthalene, 1,5-dihydroxynaphthalene, 1-naphthol, resorcinol, 2-methylresorcinol, 4-chlororesorcinol, 2-amino-3-hydroxypyridine, 3-amino-6-methoxy-2methylaminopyridine, 2,6-dihydroxy-3,4-dimethylpyridine, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-2-methylphenyl}amino)ethanol, 2,6-dihydroxy-3,4-dimethylpyridine, 1-methyl-2,6-bis(2-hydroxyethylamino)benzene, and physiologically acceptable salts thereof.

7. The agent according to claim 1, further including one or more oxidation dye precursors of the coupler type selected from the group consisting of resorcinol, 2-methylresorcinol, and 4-chlororesorcinol and one or more oxidation dye precursors of the coupler type selected from the group consisting of (2,4-diaminophenoxy)ethanol, 1,3-bis(2,4-diaminophenoxy)propane, and 1-methoxy-2-amino-4-(2-hydroxyethylamino)benzene.

8. The agent according to claim 1, further including one or more oxidation dye precursors of the coupler type selected from the group consisting of resorcinol, 2-methylresorcinol, and 4-chlororesorcinol and one or more oxidation dye precursors of the coupler type selected from the group consisting of 2-amino-3-hydroxypyridine, 3-amino-6-methoxy-2-methylaminopyridine, and 2,6-dihydroxy-3,4-dimethylpyridine.

9. The agent according to claim 1, further including one or more oxidation dye precursors of the coupler type selected from the group consisting of resorcinol, 2-methylresorcinol, and 4-chlororesorcinol and one or more oxidation dye precursors of the coupler type selected from the group consisting of 1-naphthol, 1,5-dihydroxynaphthalene, and 1-methyl-2,6-bis(2-hydroxyethylamino)benzene.

10. The agent according to claim 1, further including at least one oxidation dye precursor of the developer type selected from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine benzene, and physiologically acceptable salts thereof.

11. The agent according to claim 1, further including at least one oxidation dye precursor of the developer type selected from the group consisting of 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 4,5-diamino-1-(2-hydroxyethyl)pyrazole, and physiologically acceptable salts thereof.

12. A multicomponent kit-of-parts for oxidatively dyeing keratinic fibers, including two preparations (M1) and (M2) that are separately packaged, wherein agent (M1) is an agent according to claim 1, agent (M2) includes hydrogen peroxide in an aqueous cosmetic carrier, and the mixture of (M1) and (M2) includes hydrogen peroxide in a quantity of 0.5 to 6.0% by weight based on the total weight of the mixture of (M1) and (M2).

13. The multicomponent kit-of-parts according to claim 12, wherein the mixture of (M1) and (M2) includes water in a quantity of at least 50% by weight based on the total weight of the mixture of (M1) and (M2), and the mixture of (M1) and (M2) has a pH of 7.0 to 10.5.

* * * * *